US006403568B1

(12) United States Patent
Ohrui et al.

(10) Patent No.: US 6,403,568 B1
(45) Date of Patent: *Jun. 11, 2002

(54) 4'-C-ETHYNYL PYRIMIDINE NUCLEOSIDES AND PHARMACEUTICAL COMPOSITIONS THEREOF

(75) Inventors: Hiroshi Ohrui, Sendai; Shiro Shigeta, Fukushima; Eiichi Kodama, Kyoto; Haruhiko Machida, Choshi; Satoru Kohgo, Sendai; Hiroaki Mitsuya, Kumamoto, all of (JP)

(73) Assignee: Yamasa Corporation, Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/941,845

(22) Filed: Aug. 30, 2001

Related U.S. Application Data

(63) Continuation of application No. 09/570,041, filed on May 12, 2000, now Pat. No. 6,291,670.

(30) Foreign Application Priority Data

| May 12, 1999 | (JP) | ............................................ 11-131539 |
| Jun. 22, 1999 | (JP) | ............................................ 11-174920 |
| Nov. 9, 1999 | (JP) | ............................................ 11-318246 |
| Mar. 23, 2000 | (JP) | ............................................ 2000-81117 |

(51) Int. Cl.⁷ ..................... A61K 31/70; C07H 19/073; C07H 19/09; C07H 19/10
(52) U.S. Cl. .................... 514/49; 514/51; 536/26.8; 536/27.4; 536/28.5; 536/28.51; 536/28.52
(58) Field of Search .................... 514/49, 51; 536/27.4, 536/28.5, 28.51, 28.52, 26.8

(56) References Cited

U.S. PATENT DOCUMENTS 6,291,670 B1 * 9/2001 Ohrui et al. ................ 536/27.4

OTHER PUBLICATIONS

I. Sugimoto et al., "Nucleosides and Nucleotides. 183. Synthesis of 4'α–Branched Thymidines as a New Type of Antiviral Agent", Bioorganic & Medicinal Chemistry Letter, vol. 9, pp. 385–388, 1999. (Issue No. 3, Feb. 8, 1999).
R. Yamaguchi et al., "Synthesis of 4'–C–Ethynyl–β–D–ribo–pentofuranosyl Pyrimidines", Biosci. Biotechnol. Biochem., vol. 63, No. 4, pp. 736–742, 1999. (Apr., 1999).
S. Kohgo et al., "Synthesis of 4'–C–Ethynyl–β–D–arabino– and 4'–C–Ethynyl–2'–deoxy–β–D–ribo–pentofuranosyl Pyrimidines, and Their Biological Evaluation", Biosci. Biotechnol. Biochem., vol. 63, No. 6, pp. 1146–1149, 1999. (Jun., 1999).
M. Nomura et al., "Nucleosides and Nucleotides. 185. Synthesis and Biological Activities of 4'α–C–Branched–Chain Sugar Pyrimidine Nucleosides", J. Med. Chem. vol. 42, pp. 2901–2908, 1999. (Issue No. 15, Jul. 29, 1999).
S. Kohgo et al., "Synthesis of 4'–substituted nucleosides and their biological evaluation", Nucleic Acid Symposium Series, No. 42, pp. 127–128, Oxford Univ. Press, Maebashi, JP, Nov. 10–12, 1999.

* cited by examiner

Primary Examiner—James O. Wilson
Assistant Examiner—L. E. Crane
(74) Attorney, Agent, or Firm—Wenderoth, Lind & Ponack, L.L.P.

(57) ABSTRACT

The invention provides 4'-C-ethynyl pyrimidine nucleosides (other than 4'-C-ethynylthymidine) represented by formula [I]:

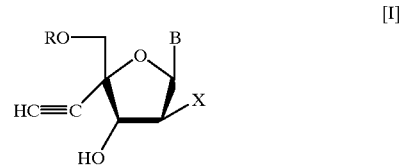

wherein B represents a base selected from the group consisting of pyrimidine and derivatives thereof; X represents a hydrogen atom or a hydroxyl group; and R represents a hydrogen atom or a phosphate residue; and a pharmaceutical composition containing any one of the compounds and a pharmaceutically acceptable carrier. Preferably, the composition is used as an anti-HIV agent or a drug for treating AIDS.

12 Claims, No Drawings

4'-C-ETHYNYL PYRIMIDINE NUCLEOSIDES AND PHARMACEUTICAL COMPOSITIONS THEREOF

This application is a continuation of U.S. application Ser. No. 09/570,041, filed on May 12, 2000, now U.S. Pat. No. 6,291,670.

BACKGROUND OF THE INVENTION

1. Field of the Invention

The present invention relates to 4'-C-ethynyl nucleosides and the use thereof for producing pharmaceuticals, and more particularly to the use thereof in treating acquired immunodeficiency syndrome (AIDS).

2. Background Art

The clinical setting for AIDS has been dramatically changed by a multi-drug therapy called highly active anti-retroviral therapy, or HAART. In this therapy, nucleoside reverse transcriptase inhibitors (NRTIs) such as zidovudine (AZT), didanosine (ddI), zalcitabine (ddC), stavudine (d4T), and lamivudine (3TC) and protease inhibitors (PIs) are employed in combination. Application of this therapy has drastically decreased the number of deaths due to AIDS in many countries (Textbook of AIDS Medicine, p751 (Williams & Wilkins, Baltimore, 1999)).

In spite of the decrease in AIDS-related deaths due to HAART, there has emerged a multi-drug resistant HIV-1 (human immunodeficiency virus-1) mutant exhibiting cross-resistance to various drugs. For example, in the early 1990s patients infected with an HIV exhibiting resistance to both AZT and 3TC were very rare, whereas the percentage of AIDS patients infected with such an HIV was as high as 42% in 1995–1996 (*AIDS*, 11, 1184(1997)).

It has been reported that such multi-drug resistant viruses cause 30–60% of drug failure cases in which the viremia level drops once below the detection limit and then revives to exhibit lasting viremia (*AIDS*, 12, 1631(1998)). Thus, the present status of *AIDS* treatment is serious.

Conventionally, in terms of a compound which exhibits potent antiviral activities against multi-drug resistant viruses, there have been known only a few protease inhibitors; e.g., JE-2147, which have potent antiviral activity against a multi-PI resistant HIV-1 (*Proc. Natl. Acad. Sci. USA*, 96,8675(1999)). However, no nucleoside derivative having such potent activities has been reported yet.

Ohrui, one of the inventors of the present invention, has synthesized 1-(4-C-ethynyl-β-D-ribo-pentofuranosyl)thymine, 4'-C-ethynyluridine, and 4'-C-ethynylcytidine and assayed biological activities such as antiviral and antitumor activities thereof. However, no such biological activities have been observed for these compounds (*Biosci. Biotechnol. Biochem.*, 63(4), 736–742, 1999).

Furthermore, Matsuda et al. have synthesized 4'-C-ethynylthymidine and assayed the anti-HIV activity thereof. The anti-HIV activity of the compound is weaker than that of AZT. However, the assay described by Matsuda et al. (*Bioorg. Med. Chem. Lett.*, 9(1999), 385–388) is drawn to an ordinary assay for determining anti-HIV activity on the basis of MT-4 cells versus an HIV-1 III$_b$ strain, and does not use a multi-drug resistant virus strain.

SUMMARY OF THE INVENTION

In order to find a compound having more potent antiviral activity than AZT, the present inventors have synthesized a variety of 4'-C-ethynyl nucleosides and evaluated the antiviral activity thereof, and have found that: 1) a 4'-ethynyl nucleoside derviative having a specific structure exhibits potent anti-HIV activity equal to or greater than that of AZT; 2) the compound has potent antiviral activity against a multi-drug resistant virus strain exhibiting resistance to various anti-HIV drugs such as AZT, ddI, ddC, d4T, and 3TC; and 3) the compound exhibits no significant cytotoxicity. The present invention has been accomplished on the basis of these findings.

Accordingly, the present invention provides 4'-C-ethynyl nucleosides (other than 4'-C-ethynylthymidine) represented by formula [I]:

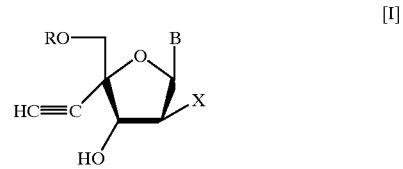

wherein B represents a base selected from the group consisting of pyrimidine, purine, and derivatives thereof; X represents a hydrogen atom or a hydroxyl group; and R represents a hydrogen atom or a phosphate residue.

The present invention also provides a pharmaceutical composition containing any one of the compounds and a pharmaceutically acceptable carrier.

Preferably, the composition is employed as an antiviral drug or a drug for treating *AIDS*.

The present invention also provides use, as pharmaceuticals, of compounds represented by formula [1].

The present invention also provides a method for treatment of *AIDS*, comprising administering a compound of formula [1] to a vertebrate, including human.

DETAILED DESCRIPTION OF PREFERRED EMBODIMENTS

(1) Compounds

The compounds of the present invention are represented by formula [I]. Examples of bases in formula [I] represented by B include pyrimidines; purines, including azapurines and deazapurines; and derivatives thereof.

Examples of substituents in the bases includes a halogen atom, an alkyl group, a haloalkyl group, an alkenyl group, a haloalkenyl group, an alkynyl group, an amino group, an alkylamino group, a hydroxyl group, a hydroxyamino group, an aminoxy group, an alkoxy group, a mercapto group, an alkylmercapto group, an aryl group, an aryloxy group, and a cyano group. The number and substitution site of these substituents are not particularly limited.

Examples of halogen atoms serving as substituents include chlorine, fluorine, iodine, and bromine. Examples of alkyl groups include C1–C7 alkyl group such as methyl, ethyl, and propyl. Examples of haloalkyl groups include C1–C7 haloalkyl groups such as fluoromethyl, difluoromethyl, trifluoromethyl, bromomethyl, and bromoethyl. Examples of alkenyl groups include C2–C7 alkenyl groups such as vinyl and allyl. Examples of haloalkenyl groups include C2–C7 haloalkenyl groups such as bromovinyl and chlorovinyl. Examples of alkynyl groups include C2–C7 alkynyl groups such as ethynyl and propynyl. Examples of alkylamino groups include C1–C7 alkylamino groups such as methylamino and ethylamino.

Examples of alkoxy groups include C1–C7 alkoxy groups such as methoxy and ethoxy. Examples of alkylmercapto groups include C1–C7 alkylmercapto groups such as methylmercapto and ethylmercapto. Examples of aryl groups include a phenyl group; alkylphenyl groups having a C1–C5 alkyl such as methylphenyl and ethylphenyl; alkoxyphenyl groups having a C1–C5 alkoxy such as methoxyphenyl and ethoxyphenyl; alkylaminophenyl groups having a C1–C5 alkyl such as dimethylaminophenyl and diethylaminophenyl; and halogenophenyl groups such as chlorophenyl and bromophenyl.

Examples of pyrimidine bases and derivatives thereof include cytosine, uracil, 5-fluorocytosine, 5-fluorouracil, 5-chlorocytosine, 5-chlorouracil, 5-bromocytosine, 5-bromouracil, 5-iodocytosine, 5-iodouracil, 5-methylcytosine, 5-ethylcytosine, 5-methyluracil (thymine), 5-ethyluracil, 5-fluoromethylcytosine, 5-fluorouracil, 5-trifluorocytosine, 5-trifluorouracil, 5-vinyluracil, 5-bromovinyluracil, 5-chlorovinyluracil, 5-ethynylcytosine, 5-ethynyluracil, 5-propynyluracil, pyrimidin-2-one, 4-hydroxyaminopyrimidin-2-one, 4-aminoxypyrimidin-2-one, 4-methoxypyrimidin-2-one, 4-acetoxypyrimidin-2-one, 4-fluoropyrimidin-2-one, and 5-fluoropyrimidin-2-one.

Examples of purine bases and derivatives thereof include purine, 6-aminopurine (adenine), 6-hydroxypurine, 6-fluoropurine, 6-chloropurine, 6-methylaminopurine, 6-dimethylaminopurine, 6-trifluoromethylaminopurine, 6-benzoylaminopurine, 6-acethylaminopurine, 6-hydroxyaminopurine, 6-aminoxypurine, 6-methoxypurine, 6-acetoxypurine, 6-benzoyloxypurine, 6-methylpurine, 6-ethylpurine, 6-trifluoromethylpurine, 6-phenylpurine, 6-mercaputopurine, 6-methylmercaputopurine, 6-aminopurine-1-oxide, 6-hydroxypurine-1-oxide, 2-amino-6-hydroxypurine (guanine), 2,6-diaminopurine, 2-amino-6-chloropurine, 2-amino-6-iodepurine, 2-aminopurine, 2-amino-6-mercaptopurine, 2-amino-6-methylmercaptopurine, 2-amino-6-hydroxyaminopurine, 2-amino-6-methoxypurine, 2-amino-6-benzoyloxypurine, 2-amino-6-acetoxypurine, 2-amino-6-methylpurine, 2-amino-6-cyclopropylaminomethylpurine, 2-amino-6-phenylpurine, 2-amino-8-bromopurine, 6-cyanopurine, 6-amino-2-chloropurine (2-chloroadenine), 6-amino-2-fluoropurine (2-fluoroadenine), 6-amino-3-deazapurine, 6-amino-8-azapurine, 2-amino-6-hydroxy-8-azapurine, 6-amino-7-deazapurine, 6-amino-1-deazapurine, and 6-amino-2-azapurine.

When B is a pyrimidine base and X is a hydrogen atom, examples of compounds represented by formula [I] include the following compounds:
4'-C-ethynyl-2'-deoxycytidine,
4'-C-ethynyl-2'-deoxy-5-halogenocytidine,
4'-C-ethynyl-2'-deoxy-5-alkylcytidine,
4'-C-ethynyl-2'-deoxy-5-haloalkylcytidine,
4'-C-ethynyl-2'-deoxy-5-alkenylcytidine,
4'-C-ethynyl-2'-deoxy-5-haloalkenylcytidine,
4'-C-ethynyl-2'-deoxy-5-alkynylcytidine,
4'-C-ethynyl-2'-deoxy-5-halogenouridine,
4'-C-ethynyl-2'-deoxy-5-alkyluridine (other than 4'-C-ethynylthymidine),
4'-C-ethynyl-2'-deoxy-5-haloalkyluridine,
4'-C-ethynyl-2'-deoxy-5-alkenyluridine,
4'-C-ethynyl-2'-deoxy-5-haloalkenyluridine, and
4'-C-ethynyl-2'-deoxy-5-alkynyluridine, and 5'-phoshate esters thereof.

When B is a pyrimidine base and X is a hydroxyl group, examples of compounds represented by formula [I] include the following compounds:
1-(4-C-ethynyl-β-D-arabino-pentofuranosyl)cytosine,
1-(4-C-ethynyl-β-D-arabino-pentofuranosyl)-5-halogenocytosine,
1-(4-C-ethynyl-β-D-arabino-pentofuranosyl)-5-alkylcytosine,
1-(4-C-ethynyl-β-D-arabino-pentofuranosyl)-5-haloalkylcytosine,
1-(4-C-ethynyl-β-D-arabino-pentofuranosyl)-5-alkenylcytosine,
1-(4-C-ethynyl-β-D-arabino-pentofuranosyl)-5-haloalkenylcytosine,
1-(4-C-ethynyl-β-D-arabino-pentofuranosyl)-5-alkynylcytosine,
1-(4-C-ethynyl-β-D-arabino-pentofuranosyl)-5-halogenouracil,
1-(4-C-ethynyl-β-D-arabino-pentofuranosyl)-5-alkyluracil,
1-(4-C-ethynyl-β-D-arabino-pentofuranosyl)-5-haloalkyluracil,
1-(4-C-ethynyl-β-D-arabino-pentofuranosyl)-5-alkenyluracil,
1-(4-C-ethynyl-β-D-arabino-pentofuranosyl)-5-haloalkenyluracil, and
1-(4-C-ethynyl-β-D-arabino-pentofuranosyl)-5-alkynyluracil, and 5'-phoshate esters thereof.

When B is a purine base and X is a hydrogen atom, examples of compounds represented by formula [I] include the following compounds:
4'-C-ethynyl-2'-deoxyadenosine,
4'-C-ethynyl-2'-deoxyguanosine,
4'-C-ethynyl-2'-deoxyinosine,
9-(4-C-ethynyl-2-deoxy-β-D-ribo-furanosyl)purine, and
9-(4-C-ethynyl-2-deoxy-β-D-ribo-furanosyl)-2,6-diaminopurine, and 5'-phoshate esters thereof.

When B is a purine base and X is a hydroxyl group, examples of compounds represented by formula [I] include the following compounds:
9-(4-C-ethynyl-β-D-arabino-pentofuranosyl)adenine,
9-(4-C-ethynyl-β-D-arabino-pentofuranosyl)guanine,
9-(4-C-ethynyl-β-D-arabino-pentofuranosyl)hypoxanthine,
9-(4-C-ethynyl-β-D-arabino-pentofuranosyl)purine, and
9-(4-C-ethynyl-β-D-arabino-pentofuranosyl)-2,6-diaminopurine, and 5'-phoshate esters thereof.

Examples of preferred compounds of the present invention includes the following compounds:
(i) 4'-C-ethynyl pyrimidine nucleosides including
  (1) a compound represented by formula [I] wherein X is a hydrogen atom,
  (2) a compound represented by formula [I] wherein X is a hydroxyl group,
  (3) a compound represented by formula [I] wherein B is cytosine,
  (4) a compound represented by formula [I] wherein B is cytosine and X is a hydrogen atom,
  (5) a compound represented by formula [I] wherein B is cytosine and X is a hydroxyl group,
  (6) 4'-C-ethynyl-2'-deoxycytidine,
  (7) 4'-C-ethynyl-2'-deoxy-5-fluorocytidine, and
  (8) 1-(4-C-ethynyl-β-D-arabinofuranosyl)cytosine, and
(ii) 4'-C-ethynyl purine nucleosides including
  (1) a compound represented by formula [I] wherein X is a hydrogen atom,
  (2) a compound represented by formula [I] wherein X is a hydroxyl group,
  (3) a compound represented by formula [I] wherein B is selected from the group consisting of adenine, guanine, hypoxanthine, and diaminopurine, (4) a compound represented by formula [I] wherein B is selected from the group consisting of adenine, guanine, hypoxanthine, and diaminopurine and X is a hydrogen atom, (5) a compound represented by formula [I] wherein B is selected from the group consisting of adenine, guanine, hypoxanthine, and diaminopurine and X is a hydroxyl group, (6) 4'-C-ethynyl-2'-deoxyadenosine, (7) 4'-C-ethynyl-2'-deoxyguanosine, (8) 4'-C-ethynyl-2'-deoxyinosine, (9) 9-(4-C-ethynyl-2-deoxy-β-D-ribo-pentofuranosyl)-2,6-diaminopurine, and

(10) 9-(4-C-ethynyl-β-D-arabino-pentofuranosyl) adenine.

The compounds of the present invention may be salts, hydrates, or solvates. When R is a hydrogen atom, examples of salts include acid-adducts such as hydrochlorides and sulfates. When R is a phosphate residue, examples of salts include alkali metal salts such as sodium salts, potassium salts, and lithium salts; alkaline earth metal salts such as calcium salts; and ammonium salts. These salts are pharmaceutically acceptable.

Examples of hydrates or solvates include adducts comprising one molecule of the compound of the present invention or a salt thereof and 0.1–3.0 molecules of water or a solvent. In addition, the compounds of the present invention encompass a variety of isomers thereof such as tautomers.

(2) Method of Production

One of the compounds of the present invention in which X is a hydrogen atom; i.e., a 2'-deoxy derivative, can be produced by the following steps.

First Step;

In the first step, a hydroxymethyl group at the 4-position of the compound represented by [II] is oxidized to thereby form an aldehyde, which is further converted into an alkyne to thereby yield a compound represented by formula [III]:

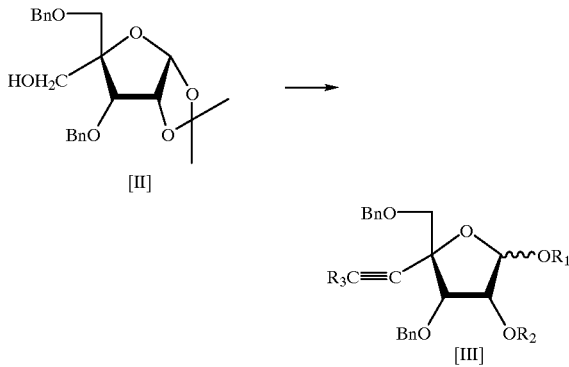

wherein each of R1 and R2 represents a protective group; R3 represents a hydrogen atom or a protective group; and Bn represents a benzyl group.

The starting material of the reaction is a known compound represented by formula [II] (Biosci. Biotech. Biochem., 57, 1433–1438(1993)).

Each of R1 and R2 may be a protective group which is typically employed for protecting a hydroxyl group. Examples of types of a protective moiety containing R1 or R2 include an ether type, an acyl type, a silyl type, and an acetal type. Specific examples protective groups include a silyl group, an acetyl group, a benzyl group, and an isopropylidenyl group.

When the hydroxymethyl group at the 4-position of the compound represented by [II] is converted into an aldehyde group by use of an oxidizing agent, examples of oxidizing agents include a chromium-containing oxidizing agent such as chromic anhydride-pyridine-acetic anhydride composite reagent, pyridinium chlorochromate, or pyridinium dichromate; a high-valency iodine oxidizing agent such as Dess-Martin reagent; and a dimethylsulfoxide-based oxidizing agent such as a combination of dimethylsulfoxide and any one of acetic anhydride, oxalyl chloride, or dicyclohexyl carbodiimide.

Reaction conditions vary depending on an employed oxidizing agent. For example, when oxidation is carried out by use of oxalyl chloride and dimethyl sulfoxide, oxalyl chloride in an amount of 0.5–5 mol and dimethyl sulfoxide in an amount of 1.5–6 mol are added to 1 mol of a compound represented by formula [II] in an organic solvent such as dichloromethane optionally under an inert gas such as argon or nitrogen. The mixture is then allowed to react for approximately 15 minutes to two hours at −100° C. to 0° C. Subsequently, a base such as triethylamine is added in an amount of 2–10 mol to the mixture, and the resultant mixture is further allowed to react at room temperature for approximately 15 minutes to two hours.

The thus-formed aldehyde can be converted into a corresponding alkyne through carbon-increasing (i.e., C—C bond formation) reaction of the aldehyde; treating the resultant compound with a strong base to thereby form a metal alkynyl compound; and introducing a protective group to the metal alkynyl compound.

Carbon-increasing reaction may be carried out in an organic solvent such as dichloromethane or dichloroethane, optionally under an inert gas such as argon or nitrogen. Specifically, 1 mol of the above-produced aldehyde is reacted with 1–5 mol of carbon tetrabromide and 2–10 mol of triphenylphosphine at 0–50° C. for approximately 15 minutes to three hours.

Treatment with a strong base may be carried out in an organic solvent such as tetrahydrofuran, 1,4-dioxane, or dimethoxyethane, optionally under an inert gas such as argon or nitrogen. Specifically, 1 mol of a compound obtained through carbon-increasing reaction is reacted with 2–4 mol of a lithium compound such as n-butyllithium or t-butyllithium at −100° C. to −20° C. for approximately 5–60 minutes.

Furthermore, when a silyl protective group represented by R3 is introduced into an alkynyl group in the thus-obtained compound, the aforementioned treatment is followed by addition of a silylating agent such as chlorotriethylsilane. A protective group can be introduced to a hydroxyl group by use of a customary method. For example, an acetyl group may be introduced through reaction with an acetylating agent such as acetic anhydride.

The thus-obtained compound represented by formula [III] may be isolated and purified through a manner which is employed for isolating and purifying typical protected saccharides. For example, the crude compound is partitioned by use of an ethyl acetate-saturated sodium bicarbonate solution, and the isolated compound is purified by use of a silica gel column.

Second step;

The second step includes condensation of a compound represented by formula [III] and a base represented by B; deoxygenation at the 2'-position; removing a protective group of a saccharide portion; and optionally phosphorylating the hydroxyl group at the 5'-position, to thereby produce a compound represented by formula [I]:

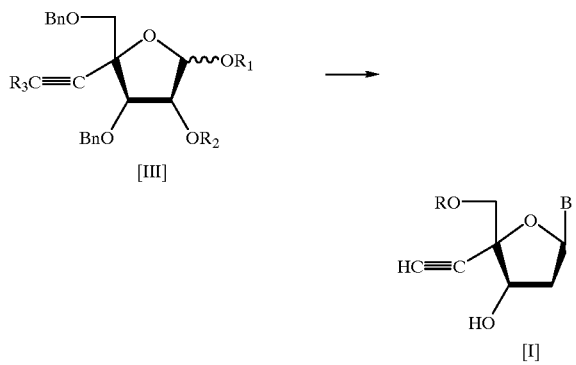

wherein B represents a base selected from the group consisting of pyrimidine; purine, including azapurine or deazapurine; and a derivative thereof (other than thymine); R represents a hydrogen atom or a phosphate residue; each of R1 and R2 represents a protective group; R3 represents a hydrogen atom or a protective group; and Bn represents a benzyl group.

Condensation of a compound represented by formula [III] and a base represented by B can be carried out by reacting the compound with the base in the presence of a Lewis acid.

The base represented by B may be silylated, and silylation may be carried out through a known method. For example, a base is silylated by use of hexamethylsilazane and trimethylchlorosilane under reflux.

Examples of Lewis acids include trimethylsilyl trifluoromethanesulfonate, tin tetrachloride, zinc chloride, zinc iodide, and anhydrous aluminum chloride.

Condensation reaction may be carried out in an organic solvent such as dichloromethane, 1,2-dichloroethane, acetonitrile, or toluene, optionally under an inert gas such as argon or nitrogen. Specifically, 1 mol of a compound represented by formula [III] is reacted with 1–10 mol of a base represented by B and 0.1–10 mol of Lewis acid at –20° C. to 150° C. for approximately 30 minutes to three hours.

Deoxygenation at the 2'-position may be carried out by converting the derivative having a hydroxyl group to the derivative having a group such as halogeno, phenoxythiocarbonyl, thiocarbonylimidazolyl, or methyldithiocarbonyl and reducing the converted derivative using a radical reducing agent in the presence of a radical initiator.

For example, when deoxygenation is carried out through phenoxythiocarbonate, conversion of a hydroxyl group to a phenoxythiocarbonyl group may be carried out in an organic solvent, such as tetrahydrofuran, acetonitrile, or dichloromethane, in the presence of a base such as dimethylaminopyridine or pyridine, optionally under an inert gas such as argon or nitrogen. Specifically, 1 mol of the aforementioned condensation product in which only the protective group for the hydroxyl group at the 2'-position had been eliminated is reacted under stirring with 1–10 mol, preferably 1.1–2 mol, of a phenyl chlorothionoformate derivative at 0–50° C. for approximately 0.5–5 hours. Alternatively, when deoxygenation is carried out via a bromo compound, the bromination may be carried out in an organic solvent, such as tetrahydrofuran, acetonitrile, or dichloromethane, by use of a brominating agent such as acetyl bromide at 0–150° C. for approximately 0.5–5 hours, optionally under an inert gas such as argon or nitrogen. The brominating agent is used in an amount of 1–50 mol, preferably 5–20 mol, per mol of the aforementioned condensate from which a protective group at the 2'-position had been removed.

Subsequently, reduction may be carried out in an organic solvent such as toluene or benzene in the presence of a radical initiator such as azobisisobutyronitrile, optionally under an inert gas such as argon or nitrogen. Specifically, 1 mol of the aforementioned phenoxythiocarbonate or bromide is reacted under stirring with 1–10 mol, preferably 2–5 mol, of a radical reducing agent such as tributyltin hydride at 50–150° C. for approximately 1–5 hours.

One of the compounds of the present invention in which X is a hydroxyl group; i.e., an arabino derivative, can be produced by the following steps.

First step;

The first step includes condensation of a compound represented by formula [III] and a base represented by B; stereochemically inverting the hydroxyl group at the 2'-position to be an arabino form; removing a protective group of a saccharide portion; and optionally phosphorylating the hydroxyl group at the 5'-position, to thereby produce a compound represented by formula [I]:

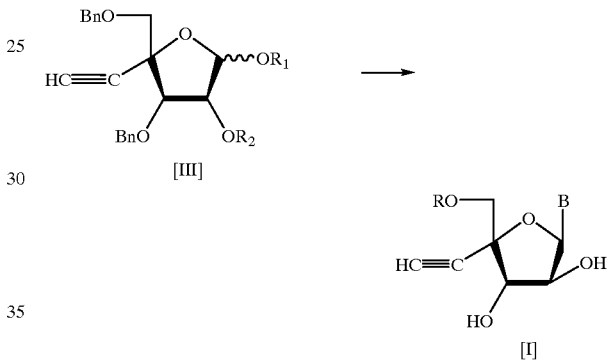

wherein B represents a base selected from the group consisting of pyrimidine, purine including azapurine or deazapurine, and a derivative thereof; R represents a hydrogen atom or a phosphate residue; each of R1 and R2 represents a protective group; R3 represents a hydrogen atom or a protective group; and Bn represents a benzyl group.

Condensation of a compound represented by formula [III] and a base represented by B can be carried out by reacting the compound with the base in the presence of a Lewis acid.

The base represented by B may be silylated, and silylation may be carried out through a known method. For example, a base is silylated by use of hexamethylsilazane and trimethylchlorosilane under reflux.

Examples of Lewis acids include trimethylsilyl trifluoromethanesulfonate, tin tetrachloride, zinc chloride, zinc iodide, and anhydrous aluminum chloride.

Condensation reaction may be carried out in an organic solvent such as dichloromethane, 1,2-dichloroethane, acetonitrile, or toluene, optionally under an inert gas such as argon or nitrogen. Specifically, 1 mol of a compound represented by formula [III] is reacted with 1–10 mol of a base represented by B and 0.1–10 mol of Lewis acid at –20° C. to 150° C. for approximately 30 minutes to three hours.

Stereo-inversion of the hydroxyl group at the 2'-position can be carried out by converting a compound containing the hydroxyl into a corresponding 2,2'-anhydrocyclonucleoside and hydrolyzing the nucleoside. Anhydrocyclization may be carried out through treatment with a sulfonating agent such as methanesulfonyl chloride, or through treatment with a fluorinating agent such as diethylaminosulfur trifluoride.

For example, when diethylaminosulfur trifluoride is employed, anhydrocyclization may be carried out in an organic solvent such as dichloromethane or toluene, optionally under an inert gas such as argon or nitrogen. Specifically, 1 mol of the aforementioned condensation product in which the protective group for the hydroxyl group at the 2'-position was removed is reacted with 1.1–5 mol, preferably 1.5–2 mol, of diethylaminosulfur trifluoride at 0° C. to room temperature for approximately five minutes to 2 hours. Alternatively, when methanesulfonyl chloride is employed, anhydrocyclization may be carried out in an organic solvent such as pyridine, optionally under an inert gas such as nitrogen. Specifically, 1 mol of the aforementioned condensation product in which the protective group for the hydroxyl group at the 2'-position had been eliminated is reacted with 1.1–5 mol, preferably 1.5–2 mol, of methanesulfonyl chloride at 0–50° C. for approximately five minutes to 10 hours.

Subsequently, hydrolysis may be carried out in the presence of an appropriate base or acid catalyst. For example, when a base catalyst is employed, hydrolysis may be carried out in a solvent mixture comprising water and an alcoholic solvent such as ethanol in the presence of a base such as sodium hydroxide or potassium hydroxide at room temperature to 100° C. for approximately 30 minutes to 5 hours.

In the case in which a base represented by B in the target compound; i.e., 4'-ethynylnucleoside, is a base having an amino group, the target compound may also be produced from a hydroxyl-containing base compound through a known method. Four example, if the 4-position of a pyrimidine base is sought to be aminated, the hydroxyl group at the 4-position of a pyrimidine base may be converted into a group such as chloro, silyloxy, alkyloxy, sulfonyloxy, or triazolyl, and then the converted group is reacted with ammonia. For example, amination through a triazole derivative may be carried out with stirring in an organic solvent such as dichloromethane, acetonitrile, dimethylformamide, or pyridine in the presence of a base such as triethylamine (triethylamine may be omitted if pyridine is used as a solvent) and a phosphorylating agent such as 4-chlorophenylphosphorodichloridate, optionally under an inert gas such as argon or nitrogen. Specifically, 1 mol of the aforementioned condensation product is reacted with 1–20 mol, preferably 2–10 mol, of 1,2,4-triazole at 0° C. to room temperature for approximately 12–72 hours, followed by addition of aqueous ammonia in an appropriate amount and further reaction at 0° C. to room temperature for approximately 1–12 hours.

In addition, an amino group in a base may be removed through a conventional method making use of any of a variety of deaminases, such as adenosine deaminase or cytidine deaminase.

Finally, a protective group of the thus-produced nucleoside is removed, to thereby obtain the compounds (R=H) of the present invention.

A protective group may be removed through a method appropriately selected from a routine procedure such as hydrolysis under acidic conditions, hydrolysis under basic conditions, treatment with tetrabutylammonium fluoride, or catalytic reduction, in accordance with the protective group employed.

When R in a target compound is a phosphate residue such as monophosphate or diphosphate, a compound in which R is a hydrogen atom is reacted with a phosphorylating agent; e.g., phosphorus oxychloride or tetrachloropyrophosphoric acid, which selectively phosphorylates the 5'-position of a nucleoside, to thereby produce a target compound in a free or salt form.

The compounds of the present invention may be isolated and purified through conventional methods, in appropriate combination, which are employed for isolating and purifying nucleosides and nucleotides; e.g., recrystallization, ion-exchange column chromatography, and adsorption column chromatography. The thus-obtained compounds may further be converted to a salt thereof in accordance with needs.

(3) Use

As shown in the below-described Test Examples, the compounds of the present invention exhibit excellent antiviral activity against herpesvirus or retrovirus. Thus, the compositions of the present invention containing one of the compounds of the present invention as an active ingredient can be used as therapeutic drugs. Specifically, the compositions of the present invention are useful for the treatment of infectious diseases caused by herpesvirus or retrovirus, in particular, AIDS, which is caused by HIV infection.

Examples of target viruses include viruses belonging to Herpesviridae such as herpes simplex virus type 1, herpes simplex virus type 2, or varicella-zoster virus, and Retroviridae such as human immunodeficiency virus.

The dose of the compounds of the present invention depends on and is determined in consideration of conditions such as the age, body weight, and type of disease of the patient; the severity of a disease of the patient; the drug tolerance; and the administration route. However, the dose per day and per body weight is selected typically within 0.00001–1,000 mg/kg, preferably 0.0001–100 mg/kg. The compounds are administered in a single or divided manner.

Any administration route may be employed, and the compounds may be administered orally, parenterally, enterally, or topically.

When a pharmaceutical is prepared from the compounds of the present invention, the compounds are typically mixed with customarily employed additives, such as a carrier and an excipient. Examples of solid carriers include lactose, kaolin, sucrose, crystalline cellulose, corn starch, talc, agar, pectin, stearic acid, magnesium stearate, lecitin, and sodium chloride. Examples of liquid carriers include glycerin, peanut oil, polyvinylpyrrolidone, olive oil, ethanol, benzyl alcohol, propylene glycol, and water.

The dosage form is arbitrarily selected. When the carrier is solid, examples of dosage forms include tablets, powder, granules, capsules, suppositories, and troches, whereas when it is liquid, examples include syrup, emulsion, soft-gelatin-encapsulated, cream, gel, paste, spray, and injection.

As shown in the below-described results of Test Examples, the compounds of the present invention exhibit excellent anti-HIV activity, particularly against multi-drug resistant HIV strains having resistance to various of anti-HIV drugs such as AZT, DDI, DDC, D4T, and 3TC. The compounds have no significant cytotoxicity. Thus, the compounds of the present invention are expected to be developed for producing pharmaceuticals, particularly drugs for treating AIDS.

EXAMPLES

The present invention will next be described in detail by way of examples including Synthesis Examples, Test Examples, and Drug Preparation Examples, which should not be construed as limiting the invention thereto.

Synthesis Example 1

(1) Synthesis of 4-C-formyl-3,5-di-O-benzyl-1,2-O-isopropylidene-α-D-ribo-pentofuranose (Compound 2)

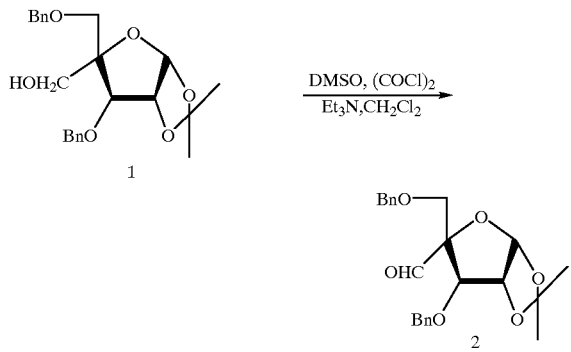

Oxalyl chloride (3.38 ml, 38.7 mmol) was dissolved in dichloromethane (80.0 ml), and dimethylsulfoxide (5.50 ml, 77.5 mmol) was added dropwise to the solution at −78° C. in an argon atmosphere, followed by stirring for 15 minutes at the same temperature. A solution (100 ml) of 4-C-hydroxymethyl-3,5-di-O-benzyl-1,2-O-isopropylidene-α-D-ribo-pentofuranose (Compound 1) (10.3 g, 25.7 mmol) in dichloromethane was added dropwise to the solution at −78° C., and the mixture was stirred for 30 minutes. After triethylamine (10.9 ml, 77.6 mmol) was added thereto, the reaction mixture was allowed to warm to room temperature, followed by stirring for 30 minutes. After water was added to the mixture with stirring, the organic layer was dried over anhydrous magnesium sulfate and was concentrated through distillation under reduced pressure. The residue was purified by means of silica gel column chromatography (silica gel 1500 ml, eluent; n-hexane:ethyl acetate=2:1), to thereby yield a colorless viscous compound (Compound 2; 9.68 g, 24.3 mmol, 94.1%).

$^1$H-NMR(CDCl$_3$) δ9.92 (1H, s, formyl), 7.33–7.24 (10H, m, aromatic), 5.84 (1H, d, H-1 $J_{1,2}$=3.30), 4.71, 4.59 (each 1H, d, benzyl, $J_{gem}$=12.00), 4.60 (1H, br.t, H-2), 4.52, 4.46 (each 1H, d, benzyl, $J_{gem}$=12.00), 4.37 (1H, d, H-3, $J_{2,3}$=4.50), 3.68, 3.61 (each 1H, d, H-5, $J_{gem}$=10.95), 1.60, 1.35 (each 3H, s, acetonide)

EIMS m/z: 398(M$^+$).

HRMS m/z(M$^+$): Calcd. for C$_{23}$H$_{26}$O$_6$: 398.1729, Found: 398.1732

[α]$_D$+24.5° (c=1.03, CHCl$_3$)

(2) Synthesis of 4-C-(2,2-dibromoethenyl)-3,5-di-O-benzyl-1,2-O-isopropylidene-α-D-ribo-pentofuranose (Compound 3)

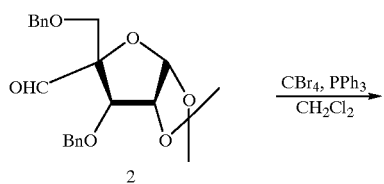

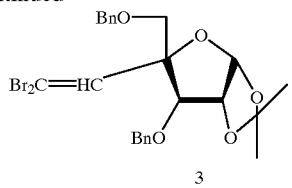

Compound 2 (9.50 g, 23.8 mmol) was dissolved in dichloromethane (200 ml), and carbon tetrabromide (15.8 g, 47.6 mmol) and triphenylphosphine (25.0 g, 95.3 mmol) were added to the solution under ice-cooling, followed by stirring at room temperature for one hour. Triethylamine (20.0 ml, 142 mmol) was added to the mixture, followed by stirring for 10 minutes. The reaction mixture was poured into n-hexane (1000 ml) and the produced precipitates were separated through filtration. The filtrate was concentrated through distillation under reduced pressure, and the residue was purified by means of silica gel column chromatography (silica gel 1500 ml, eluent; n-hexane:ethyl acetate=3:1), to thereby yield a colorless viscous compound (Compound 3; 12.6 g, 22.7 mmol, 95.4%).

$^1$H-NMR(CDCl$_3$) δ7.34–7.24 (10H, m, aromatic), 7.16 (1H, s, Br$_2$C=CH—), 5.76 (1H, d, H-1 $J_{1,2}$=3.90), 4.72, 4.60 (each 1H, d, benzyl, $J_{gem}$=12.00), 4.53 (1H, br.t, H-2), 4.60, 4.42 (each 1H, d, benzyl, $J_{gem}$=12.00), 4.21 (1H, d, H-3, $J_{2,3}$=4.80), 3.83, 3.39 (each 1H, d, H-5, $J_{gem}$=11.40), 1.59, 1.30 (each 3H, s, acetonide)

EIMS m/z: 473, 475 (M-Br).

[α]$_D$+6.20° (c=1.00, CHCl$_3$)

(3) Synthesis of 4-C-ethynyl-3,5-di-O-benzyl-1,2-O-isopropylidene-α-D-ribo-pentofuranose (Compound 4)

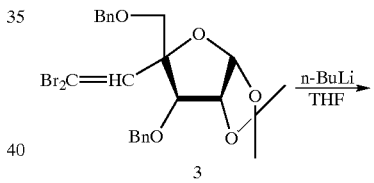

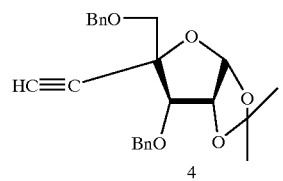

Compound 3 (12.4 g, 22.4 mmol) was dissolved in dry tetrahydrofuran (160 ml), and a 1.6 M n-butyl lithium (30.7 ml, 49.1 mmol) in n-hexane was added to the solution at −78° C. in an argon atmosphere, followed by stirring for 30 minutes at the same temperature. After water was added to the mixture with stirring, the organic layer was dried over anhydrous magnesium sulfate and concentrated through distillation under reduced pressure. The residue was purified by means of silica gel column chromatography (silica gel 1500 ml, eluent; n-hexane:ethyl acetate=3:1), to thereby yield a colorless viscous compound (Compound 4; 7.95 g, 20.2 mmol, 90.3%).

$^1$H-NMR(CDCl$_3$) δ7.39–7.22 (10H, m, aromatic), 5.70 (1H, d, H-1 $J_{1,2}$=3.60), 4.78, 4.69 (each 1H, d, benzyl, $J_{gem}$=12.60), 4.55 (1H, br.t, H-2), 4.53, 4.44 (each 1H, d, benzyl, $J_{gem}$=12.30), 4.16 (1H, d, H-3, $J_{2,3}$=4.50), 3.71, 3.56 (each 1H, d, H-5, $J_{gem}$=11.40), 1.73, 1.33 (each 3H, s, acetonide)

EIMS m/z: 394(M+).
HRMS m/z(M+): Calcd. for $C_{24}H_{26}O_5$: 394.1780, Found: 394.1777
$[\alpha]_D$+22.60 (c=1.00, $CHCl_3$)
(4) Synthesis of 4-C-triethylsilylethynyl-3,5-di-O-benzyl-1,2-O-isopropylidene-α-D-ribo-pentofuranose (Compound 5)

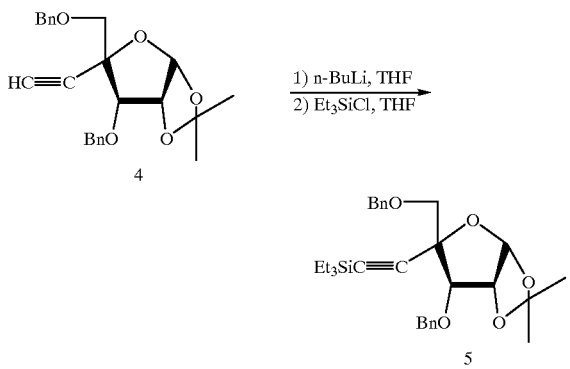

Compound 4 (5.00 g, 12.7 mmol) was dissolved in dry tetrahydrofuran (100 ml), and a 1.6 M n-butyl lithium (9.50 ml, 15.2 mmol) in n-hexane was added to the solution at −78° C. in an argon atmosphere, followed by stirring for five minutes at the same temperature. Under the same conditions, chlorotriethylsilane (2.55 ml, 15.2 mmol) was added thereto, followed by stirring for 30 minutes. After water was added to the mixture with stirring, the organic layer was dried over anhydrous magnesium sulfate and concentrated through distillation under reduced pressure. The residue was purified by means of silica gel column chromatography (silica gel 1000 ml, eluent; n-hexane:ethyl acetate=3:1), to thereby yield a colorless oily compound (Compound 5; 6.32 g, 12.4 mmol, 97.6%).

$^1$H-NMR($CDCl_3$) δ7.41-7.22 (10H, m, aromatic), 5.71 (1H, d, H-1, $J_{1,2}$=3.85), 4.77, 4.65 (each 1H, d, benzyl, $J_{gem}$=12.09), 4.63 (1H, br.t, H-2), 4.57, 4.48 (each 1H, d, benzyl, $J_{gem}$=12.09), 4.23 (1H, d, H-3, $J_{2,3}$=4.67), 1.73, 1.33 (each 3H, s, acetonide), 0.98 (9H, t, Si—$CH_2$—$CH_3$, J=7.83), 0.60 (6H, Si—$CH_2$—$CH_3$, J=7.97)

EIMS m/z: 508(M+).
HRMS m/z(M+): Calcd. for $C_{30}H_{40}O_5Si$: 508, 2645, Found: 508,2642
$[\alpha]_D$-27.27° (c=1.045, $CHCl_3$)
(5) Synthesis of 4-C-triethylsilylethynyl-1,2-di-O-acetyl-3,5-di-O-benzyl-D-ribo-pentofuranose (Compound 6)

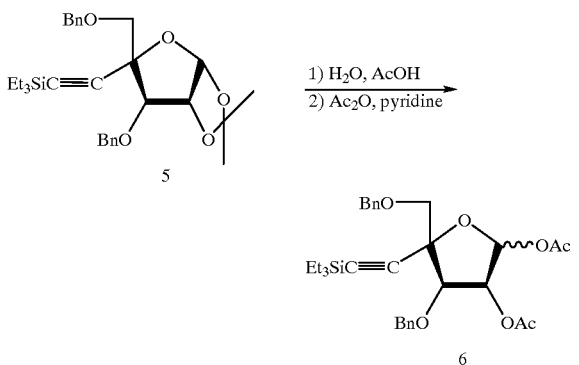

Compound 5 (5.55 g, 10.9 mmol) was dissolved in acetic acid (70.0 ml), and trifluoroacetic acid (10.0 ml) and water (30.0 ml) were added to the solution, followed by stirring overnight at room temperature. After disappearance of Compound 5 had been confirmed by means of silica gel thin-layer chromatography, the reaction mixture was concentrated through distillation under reduced pressure. The residue was further concentrated by co-boiling with toluene three times, and then dissolved in pyridine (50.0 ml). Acetic anhydride (10.3 ml, 0.11 mol) was added thereto, followed by stirring overnight at room temperature. The reaction mixture was concentrated through distillation under reduced pressure, and the residue was dissolved in ethyl acetate. The organic layer was washed with water, dried over anhydrous magnesium sulfate, and concentrated through distillation under reduced pressure. The residue was purified by means of silica gel column chromatography (silica gel 1000 ml, eluent; n-hexane:ethyl acetate=5:1), to thereby yield a colorless viscous compound (Compound 6; 4.80 g, 8.68 mmol, 79.6%) as an anomer mixture (α:β=1:6.6).

$^1$H-NMR for α anomer ($CDCl_3$) δ7.38-7.28 (10H, m, aromatic), 6.39 (1H, d, H-1, $J_{1,2}$=4.67), 5.13 (1H, dd, H-2, $J_{1,2}$=4.67, $J_{2,3}$=6.87), 4.80, 4.55 (each 1H, benzyl, d, $J_{gem}$=12.09), 4.61, 4.52 (each 1H, d, benzyl, $J_{gem}$=12.09), 4.30 (1H, d, H-3, $J_{2,3}$=6.87), 3.62 (2H, d, H-5, J=0.55), 2.12, 2.07 (each 3H, s. acetyl), 0.94 (9H, t, Si—$CH_2$—$CH_3$, J=7.97), 0.55 (6H, Si—$CH_2$—$CH_3$, J=7.97)
$[\alpha]_D$-21.8° (c=1.00, $CHCl_3$)
$^1$H-NMR for β anomer ($CDCl_3$) δ7.35-7.24 (10H, m, aromatic), 6.20 (1H, d, H-1, $J_{1,2}$=0.82), 5.33 (1H, dd, H-2, $J_{1,2}$=0.82, $J_{2,3}$=4.67), 4.66, 4.61 (each 1H, benzyl, d, $J_{gem}$=11.81), 4.56, 4.47 (each 1H, benzyl, d, $J_{gem}$=11.81), 4.48 (1H, d, H-3, $J_{2,3}$=4.67), 3.69, 3.62 (each 1H, d, H-5, $J_{gem}$=10.99), 2.09, 1.84 (each 3H, s. acetyl), 0.96 (9H, t, Si—$CH_2$—$CH_3$, J=7.97), 0.58 (6H, Si—$CH_2$—$CH_3$, J=7.97)
$[\alpha]_D$-58.0° (c=1.00, $CHCl_3$)
EIMS m/z: 552(M+).
HRMS m/z(M+): Calcd. for $C_{31}H_{40}O_7Si$: 552.2543, Found: 552.2551
(6) Synthesis of 4'-C-triethylsilylethynyl-2'-O-acetyl-3',5'-di-O-benzyluridine (Compound 7)

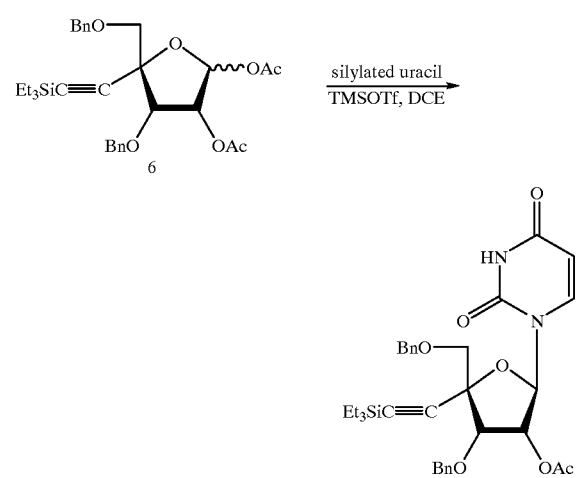

Compound 6 (3.00 g, 5.43 mmol) was dissolved in 1,2-dichloroethane (100 ml), and uracil (1.52 g, 13.6 mmol) and N,O-bis(trimethylsilyl)acetamide (9.40 ml, 38.0 mmol) were added to the solution, followed by refluxing for one hour. After the reaction mixture was allowed to cool to room temperature, trimethylsilyl trifluoromethanesulfonate (1.97 ml, 10.9 mmol) was added thereto, followed by stirring overnight at 50° C. A saturated aqueous solution of sodium hydrogencarbonate was added to the mixture, and after stirring, precipitate was filtered. The organic layer was dried over anhydrous magnesium sulfate and concentrated through distillation under reduced pressure. The residue was purified by means of silica gel column chromatography (silica gel 300 ml, eluent; n-hexane:ethyl acetate=1:1), to thereby yield a colorless viscous compound (Compound 7; 2.50 g, 4.13 mmol, 76.1%).

$^1$H-NMR(CDCl$_3$) δ8.63 (1H, br.s, 3-NH), 7.59 (1H, d, 6-H, J$_{5',6}$=8.24), 7.41-7.24 (10H, m, aromatic), 6.31 (1H, d, H-1', J$_{1',2'}$=4.95), 5.34 (1H, d, H-5, J$_{5,6}$=8.24), 5.21 (1H, dd, H-2', J$_{1',2'}$=4.95, J$_{2',3'}$=6.04), 4.71, 4.58 (each 1H, d, benzyl, J$_{gem}$=11.81), 4.48 (2H, s, benzyl), 4.34 (1H, d, H-3', J$_{2',3'}$=6.04), 3.86, 3.67 (each 1H, d, H-5', J$_{gem}$=10.50), 2.05 (3H, s, acetyl), 0.97 (9H, t, Si—CH$_2$—CH$_3$, J=7.95), 0.60 (6H, Si—CH$_2$—CH$_3$, J=7.95).

FABMS m/z: 605(MH$^+$).

HRMS m/z(MH$^+$): Calcd. for C$_{33}$H$_{41}$N$_2$O$_7$Si: 605.2683, Found: 605.2683.

[α]$_D$-21.97° (c=1.015, CHCl$_3$).

(7) Synthesis of 4'-C-triethylsilylethynyl-3',5'-di-O-benzyluridine (Compound 8)

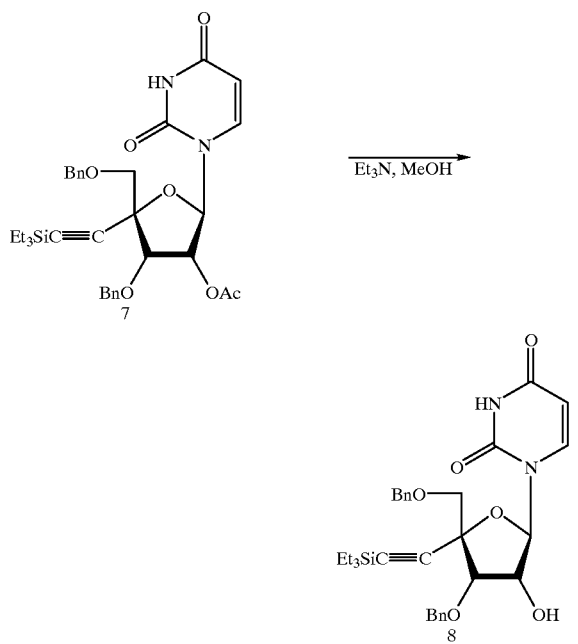

Compound 7 (2.00 g, 3.3 mmol) was dissolved in methanol (90.0 ml), and triethylamine (10.0 ml) was added to the solution, followed by stirring for 48 hours at room temperature. The reaction mixture was concentrated through distillation under reduced pressure, and the residue was purified by means of silica gel column chromatography (silica gel 200 ml, eluent; n-hexane:ethyl acetate=1:1), to thereby yield a white powdery compound (Compound 8; 1.72 g, 3.06 mmol, 92.4%).

$^1$H-NMR(CDCl$_3$) δ8.43 (1H, br.s, 3-NH), 7.55 (1H, d, H-6, J$_{5',6}$=8.24), 7.41-7.25 (10H, m, aromatic), 6.10 (1H, d, H-1', J$_{1',2'}$5.22), 5.37 (1H, dd, H-5, J$_{5',6'}$=8.24), 4.96, 4.66 (each 1H, d, benzyl, J$_{gem}$=11.54), 4.56, 4.50 (each 1H, d, benzyl, J$_{gem}$=11.00), 4.21 (1H, m, H-2'), 4.17 (1H, d, H-3', J$_{2',3'}$=5.77), 3.87, 3.74 (each 1H, d, H-5', J$_{gem}$=10.44), 3.02 (1H, br.d, 2'-OH), 0.97 (9H, t, Si—CH$_2$—CH$_3$, J=7.69), 0.60 (6H, Si—CH$_2$—CH$_3$, J=7.69).

FABMS m/z: 563(MH$^+$).

HRMS m/z(MH$^+$): Calcd. for C$_{31}$H$_{39}$N$_2$O$_6$Si: 563.2577, Found: 563.2586.

[α]$_D$-21.56° (c=1.025, CHCl$_3$)

m.p. 119–120° C.

(8) Synthesis of 4'-C-triethylsilylethynyluridine (Compound 9)

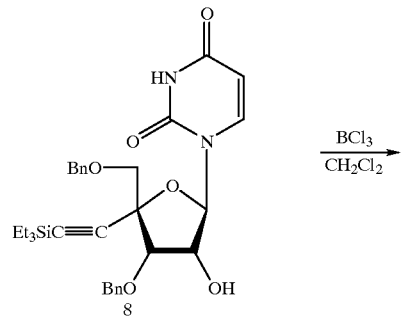

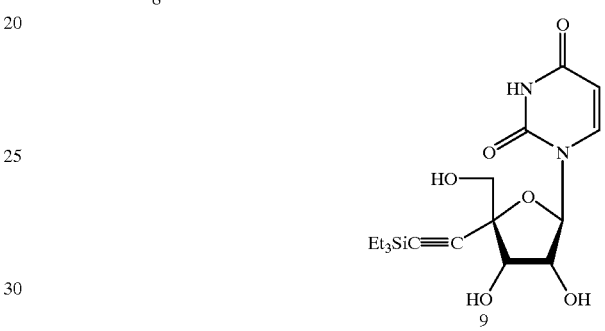

Compound 8 (1.50 g, 2.67 mmol) was dissolved in dichloromethane (75.0 ml), and a 1.0 M boron trichloride (26.7 ml, 26.7 mmol) in dichloromethane was added to the solution at −78° C. in an argon atmosphere, followed by stirring for three hours at the same temperature. A mixture of pyridine (10.0 ml) and methanol (20.0 ml) was added thereto at −78° C., followed by stirring for ten minutes. The reaction mixture was concentrated through distillation under reduced pressure, and the residue was partitioned with ethyl acetate and water. The organic layer was dried over anhydrous magnesium sulfate and concentrated through distillation under reduced pressure. The residue was purified by means of silica gel column chromatography (silica gel 200 ml, eluent; chloroform:methanol=9:1), to thereby yield a white powdery compound (Compound 9; 0.95 g, 2.48 mmol, 92.9%).

$^1$H-NMR(CDCl$_3$) δ11.36 (1H, d, 3-NH), 7.81 (1H, d, H-6, J$_{5,6}$=8.24), 5.92 (1H, d, H-1', J$_{1',2'}$=6.32), 5.68 (1H, dd, J$_{5,6}$=8.24), 5.55 (1H, t, 5'-OH), 5.33 (1H, d, 2'-OH), 5.16 (1H, d, 3'-OH), 4.13 (1H, dd, H-2', J$_{1',2'}$=6.32, J$_{2',3'}$=5.77) 4.07 (1H, t, H-3', J$_{2',3'}$=5.77), 3.58 (1H, d, H-5'), 0.96 (9H, t, Si—CH$_2$—CH$_3$, J=7.97), 0.57 (6H, Si—CH$_2$—CH$_3$, J=7.97).

FABMS m/z: 383(MH$^+$).

HRMS m/z(MH$^+$): Calcd. for C$_{17}$H$_{27}$N$_2$O$_6$Si: 383, 1638, Found: 383.1645.

[α]$_D$-4.50° (c=1.00, CH$_3$OH)

m.p. 183–186° C.

(9) Synthesis of 4'-C-triethylsilylethynyl-3',5'-di-O-acetyl-2'-deoxyuridine (Compound 11)

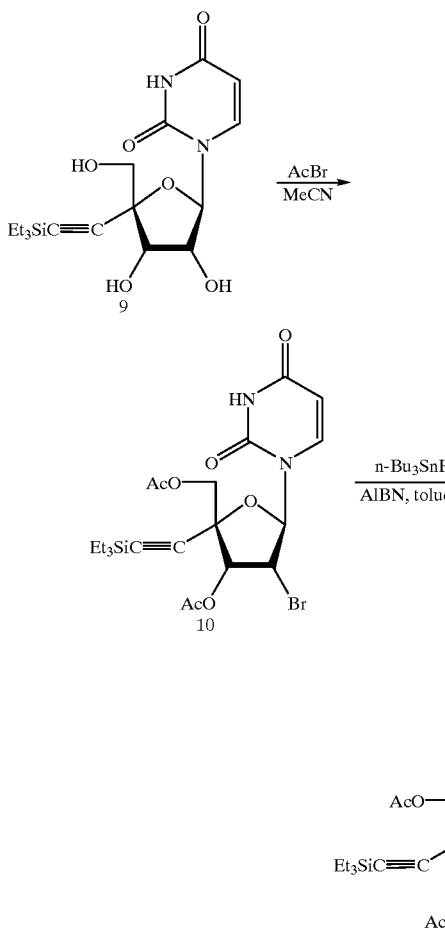

Compound 9 (0.80 g, 2.09 mmol) was suspended in acetonitrile (20.0 ml), and a solution (20.0 ml) of acetyl bromide (1.55 ml, 21.0 mmol) in acetonitrile was added dropwise to the suspension at 85° C. over 30 minutes, followed by refluxing for one hour. After the reaction mixture was concentrated through distillation under reduced pressure, the residue was dissolved in ethyl acetate and the solution was washed with a saturated aqueous solution of sodium hydrogencarbonate and a saturated aqueous solution of sodium chloride. The organic layer was dried over anhydrous magnesium sulfate and concentrated through distillation under reduced pressure, to thereby yield 4'-C-triethylsilylethynyl-3',5'-di-O-acetyl-2'-bromo-2'-deoxyuridine (Compound 10). After the crude product (Compound 10) was concentrated by co-boiling with toluene three times, the product was dissolved in dry toluene (50.0 ml). Hydrogenated tri(n-butyl)tin (1.08 ml, 4.19 mmol) and 2,2'-azobis(isobutyronitrile) (0.01 g) were added to the solution at 85° C., and the mixture was heated under stirring for one hour in an argon atmosphere. After the reaction mixture was concentrated through distillation under reduced pressure, the residue was purified by means of silica gel column chromatography (silica gel 300 ml, eluent; toluene: ethyl acetate), to thereby yield a colorless viscous compound (Compound 11; 0.40 g, 42.6%).

$^1$H-NMR(CDCl$_3$) δ7.49 (1H, d, H-6, J$_{5,6}$=8.24), 6.34 (1H, t, H-1', J$_{1',2'}$=6.46), 5.77 (1H, dd, H-5, J$_{5,6}$=8.24), 5.37 (1H, dd, H-3', J$_{2',3'}$=4.95, 7.42), 4.42, 4.37 (each 1H, d, H-5', J$_{gem}$=11.81), 2.62, 2.32 (each 1H, m, H-2'), 2.13 (6H, s, acetyl), 1.00 (9H, t, Si—CH$_2$—CH$_3$, J=7.82), 0.63 (6H, Si—CH$_2$—CH$_3$, J=7.82).

FABMS m/z: 451(MH$^+$).

HRMS m/z(MH$^+$): Calcd. for C$_{21}$H$_{31}$N$_2$O$_7$Si: 451.1900, Found: 451.1934.

[α]$_D$ –11.7° (c=1.04, CHCl$_3$)

(10) Synthesis of 4'-C-ethynyl-2'-deoxycytidine (Compound 13)

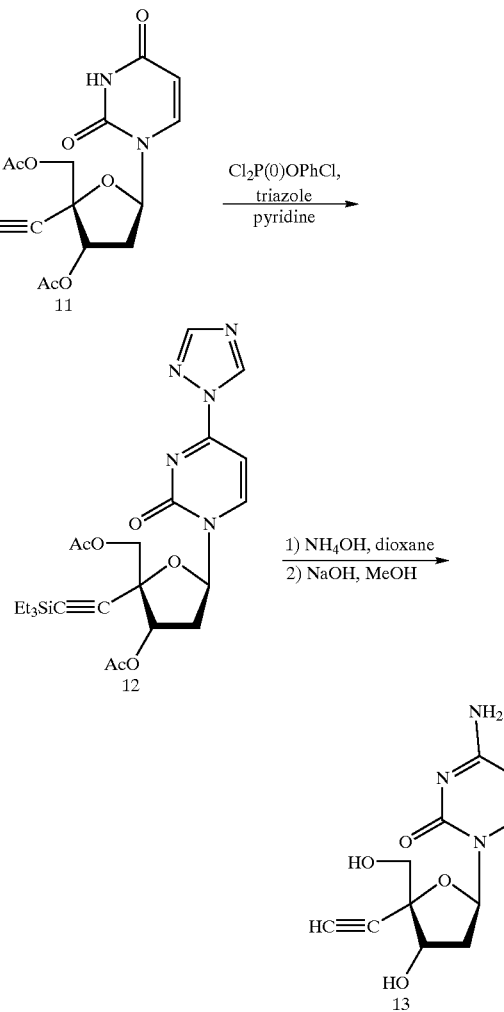

Compound 11 (0.30 g, 0.67 mmol) was dissolved in pyridine (15.0 ml), and p-chlorophenylphosphrodichloridate (0.33 ml, 2.00 mmol) was added to the solution under ice-cooling, followed by stirring for two minutes. 1,2,4-Triazole (0.46 g, 6.66 mmol) was added to the mixture, followed by stirring for seven days at room temperature. After disappearance of raw material had been confirmed by means of silica gel thin-layer chromatography, the reaction mixture was concentrated through distillation under reduced pressure, and the residue was partitioned with ethyl acetate and water. The organic layer was dried over anhydrous magnesium sulfate and concentrated through distillation under reduced pressure. The residue was purified by means of silica gel column chromatography (silica gel 50 ml, eluent; n-hexane:ethyl acetate=1:3), to thereby yield colorless viscous Compound 12: 4-(1,2,4-triazolo)-4'-C-ethynyl-2'-deoxyuridine. Compound 12 was dissolved in dioxane (30.0 ml), and 25% aqueous ammonia (10.0 ml) was added to the solution, followed by stirring overnight at room temperature. After disappearance of Compound 12 had been confirmed by means of silica gel thin-layer chromatography, the reaction mixture was concentrated through distillation under reduced pressure. The residue was dissolved in methanol (45.0 ml), and an aqueous 1 N solution of sodium hydroxide (5.00 ml, 5.00 mmol) was added thereto, followed by stirring for two hours at room temperature. Acetic acid (0.29 ml, 5.00 mmol) was added to the mixture, and the reaction mixture was concentrated through distillation under reduced pressure. The residue was purified by means of reversed-phase medium-pressure column chromatography (Wakosil 40C18 50 g, eluent; a 5% aqueous solution of acetonitrile). The fractions containing Compound 13 were brought to dryness under reduced pressure, and the residue was crystallized from methanol-ether, to thereby yield a white crystalline compound (Compound 13; 0.12 g, 0.48 mmol, 71.6%).

$^1$H-NMR(DMSO-d$_6$) δ7.78 (1H, d, H-6, J$_{5,6}$=7.50), 7.17 (2H, br.d, NH$_2$), 6.14 (1H, dd, H-1', J$_{1',2'}$=4.76, 7.20), 5.72 (1H, d, H-5, J$_{5,6}$=7.50), 5.49 (1H, d, 3'-OH), 5.42 (1H, t, 5'-OH), 4.30 (1H, t, H-3', J$_{2',3'}$32 7.20), 3.64, 3.58 (each 1H, m, H-5'), 3.48 (1H, s, ethynyl), 2, 25, 2.07 (each 1H, m, H-2')

[α]$_D$+75.0° (c=1.00, CH$_3$OH)

FABMS m/z: 252(MH$^+$).

HRMS m/z(MH$^+$): Calcd. for C$_{11}$H$_{14}$N$_3$O$_4$: 252.0984, Found: 252.0979.

UV λ max (CH$_3$OH) nm (ε): 271 (9227)

m.p. 220° C. (Dec)

Synthesis Example 2

5-Fluorouracil, 5-ethyluracil, 5-bromovinyluracil, and 5-ethynyluracil were employed instead of uracil used in Synthesis Example 1 (6), and the reactions were carried out in the same manner as described above (if necessary, amination reaction by use of triazole described in (10) was omitted), to thereby synthesize the following compounds:

4'-C-ethynyl-2'-deoxy-5-fluorouridine;
4'-C-ethynyl-2'-deoxy-5-ethyluridine;
4'-C-ethynyl-2'-deoxy-5-bromovinyluridine;
4'-C-ethynyl-2'-deoxy-5-ethynyluridine;
4'-C-ethynyl-2'-deoxy-5-ethylcytidine;
4'-C-ethynyl-2'-deoxy-5-bromovinylcytidine; and
4'-C-ethynyl-2'-deoxy-5-ethynylcytidine.

Synthesis Example 3

(1) Synthesis of 4-C-ethynyl-1,2-di-O-acetyl-3,5-di-O-benzyl-D-ribo-pentofuranose (Compound 14)

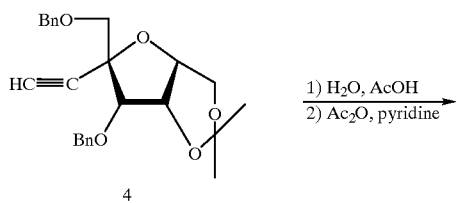
4

1) H$_2$O, AcOH
2) Ac$_2$O, pyridine
→

-continued

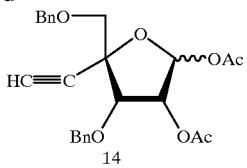
14

Compound 4 (6.00 g, 15.2 mmol) was dissolved in acetic acid (70.0 ml), and trifluoroacetic acid (10.0 ml) and water (30.0 ml) were added to the solution, followed by stirring overnight at room temperature. After disappearance of Compound 4 had been confirmed by means of silica gel thin-layer chromatography, the reaction mixture was concentrated through distillation under reduced pressure. The residue was concentrated by co-boiling with toluene three times. The treated residue was dissolved in pyridine (50.0 ml). Acetic anhydride (14.3 ml, 0.15 mol) was added thereto, followed by stirring overnight at room temperature. The reaction mixture was concentrated through distillation under reduced pressure, and the residue was dissolved in ethyl acetate. The organic layer was washed with water, dried over anhydrous magnesium sulfate, and concentrated through distillation under reduced pressure. The residue was purified by means of silica gel column chromatography (silica gel 1000 ml, eluent; n-hexane:ethyl acetate=2:1), to thereby yield a colorless viscous compound (Compound 14; 5.40 g, 12.3 mmol, 80.9%) as an anomer mixture (α:β=1:3.0).

$^1$H-NMR for α anomer (CDCl$_3$) δ7.39-7.25 (10H, m, aromatic), 6.42 (1H, d, H-1, J$_{1,2}$=4.67), 5.13 (1H, dd, H-2, J$_{1,2}$=4.67, J$_{2,3}$=6.87), 4.81, 4.60 (each 1H, benzyl, d, J$_{gem}$=12.09), 4.59, 4.51 (each 1H, d, benzyl, J$_{gem}$=12.09), 4.30 (1H, d, H-3, J$_{2,3}$=6.87), 3.63 (2H, d, H-5, J=0.55), 2.73 (1H, s, ethynyl), 2.10, 2.02 (each 3H, s. acetyl).

$^1$H-NMR for β anomer (CDCl$_3$) δ7.35-7.20 (10H, m, aromatic), 6.21 (1H, d, H-1, J$_{1,2}$=0.82), 5.40 (1H, dd, H-2, J$_{1,2}$=0.82, J$_{2,3}$=4.67), 4.66, 4.60 (each 1H, benzyl, d, J$_{gem}$=11.81), 4.50, 4.47 (each 1H, benzyl, d, J$_{gem}$=11.81), 4.42 (1H, d, H-3, J$_{2,3}$=4.67), 3.70, 3.66 (each 1H, d, H-5, J$_{gem}$=10.99), 2.80 (1H, s, ethynyl), 2.08, 1.81 (each 3H, s. acetyl).

EIMS m/z: 438(M$^+$).

HRMS m/z(M$^+$): Calcd. for C$_{25}$H$_{26}$O$_7$: 438.1679, Found: 438.1681

(2) Synthesis of 4'-C-ethynyl-2'-O-acetyl-3',5'-di-O-benzyluridine (Compound 15)

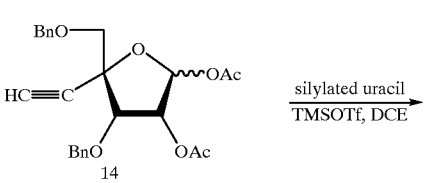
14 silylated uracil
────────
TMSOTf, DCE

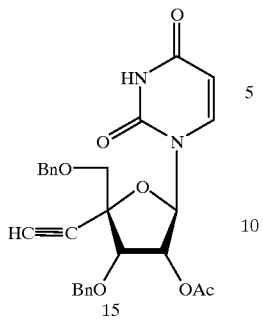

Compound 14 (2.50 g, 5.70 mmol) was dissolved in 1,2-dichloroethane (80.0 ml), and uracil (1.60 g, 14.27 mmol) and N,O-bis(trimethylsilyl)acetamide (9.86 ml, 39.74 mmol) were added to the solution, followed by refluxing for one hour. After the reaction mixture was allowed to cool to room temperature, trimethylsilyl trifluoromethanesulfonate (2.06 ml, 11.40 mmol) was added thereto, followed by stirring overnight at 50° C. A saturated aqueous solution of sodium hydrogencarbonate was added to the mixture, and after stirring, precipitate was filtered. The organic layer was dried over anhydrous magnesium sulfate and concentrated through distillation under reduced pressure. The residue was purified by means of silica gel column chromatography (silica gel 300 ml, eluent; n-hexane:ethyl acetate=2:3), to thereby yield a colorless viscous compound (Compound 15; 2.44 g, 4.97 mmol, 87.2%).

$^1$H-NMR(CDCl$_3$) δ8.52 (1H, br. s, 3-NH), 7.55 (1H, d, 6-H, $J_{5,6}$=8.24), 7.40-7.22 (10H, m, aromatic), 6.25 (1H, d, H-1', $J_{1',2'}$=4.40), 5.33 (1H, d, H-5, $J_{5,6}$=8.24), 5.22 (1H, dd, H-2', $J_{1',2'}$=4.40, $J_{2',3'}$=5,77), 4.63 (2H, s, benzyl), 4.45, 4.40 (each 1H, d, benzyl, $J_{gem}$=10.99), 4.34 (1H, d, H-3', $J_{2',3'}$=5.77), 3.84, 3.62 (each 1H, d, H-5', $J_{gem}$=10.58), 2.69 (1H, s, ethynyl), 2.11 (3H, s, acetyl).

FABMS m/z: 491(MH$^+$).

HRMS m/z(MH$^+$): Calcd. for C$_{27}$H$_{27}$N$_2$O$_7$: 491.1818, Found: 491.1821.

[α]$_D$29.0° (c=1.00, CHCl$_3$).

(3) Synthesis of 1-(4-C-ethynyl-2-O-acetyl-3,5-di-O-benzyl-β-D-arabino-pentofuranosyl)uracil (Compound 16)

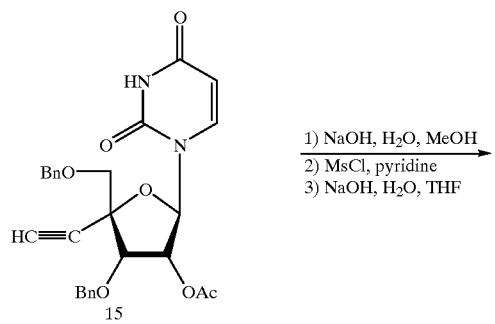

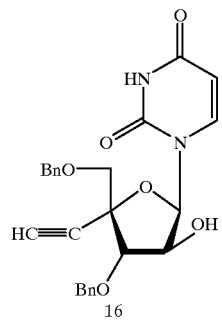

Compound 15 (2.30 g, 4.69 mmol) was dissolved in methanol (90.0 ml), and a 1 N aqueous solution of sodium hydroxide (10.0 ml) was added to the solution, followed by stirring for two hours at room temperature. The reaction mixture was neutralized with acetic acid and then brought to dryness under reduced pressure. The residue was dissolved in ethyl acetate. The organic layer was washed with water, dried over anhydrous magnesium sulfate, and brought to dryness under reduced pressure. The residue was concentrated by co-boiling with a small amount of pyridine three times. The product was dissolved in pyridine (50.0 ml), and methanesulfonyl chloride (0.73 ml, 9.41 mmol) was added to the solution under cooling, followed by stirring for three hours. A small amount of water was added to the reaction mixture, and the mixture was brought to dryness under reduced pressure. The residue was dissolved in ethyl acetate, followed by washing with water. The organic layer was dried over anhydrous magnesium sulfate and then brought to dryness under reduced pressure. The residue was dissolved in tetrahydrofuran (30.0 ml), and a 1 N aqueous solution of sodium hydroxide (50.0 ml) was added to the solution, followed by refluxing for one hour. After the reaction mixture was neutralized with acetic acid, the target compound was taken up through extraction with ethyl acetate. The organic layers were combined and dried over anhydrous magnesium sulfate. The organic layer was brought to dryness under reduced pressure, and the residue was purified by means of silica gel column chromatography (silica gel 250 ml, eluent; n-hexane:ethyl acetate=1:2), to thereby yield a white powder compound (Compound 16; 1.54 g, 3.43 mmol, 73.1%).

$^1$H-NMR(CDCl$_3$) δ9.82 (1H, br.s, 3-NH), 7.73 (1H, d, 6-H, $J_{5,6}$=8.06), 7.41-7.19 (10H, m, aromatic), 6.24 (1H, d, H-1', $J_{1',2'}$=5,86), 5.25 (1H, d, H-5, $J_{5,6}$=8.06), 4.88, 4.76 (each 1H, d, benzyl, $J_{gem}$=12.21), 4.78 (1H, H-2'), 4.52 (1H, 2'-OH), 4.46, 4.39 (each 1H, d, benzyl, $J_{gem}$=11.11), 4.19 (1H, d, H-3, $J_{2',3'}$=6.59), 3.834, 3.64 (each 1H, d, H-5', $J_{gem}$=10.62), 2.67 (1H, s, ethynyl).

FABMS m/z: 449(MH$^+$).

HRMS m/z(MH$^+$): Calcd. for C$_{25}$H$_{25}$N$_2$O$_6$: 449.1712, Found: 449.1713.

[α]$_D$40.70 (c=1.00, CHCl$_3$).

m.p. 105–106° C.

(4) Synthesis of 1-(4-C-ethynyl-2,3,5-tri-O-acetyl-β-D-arabino-pentofuranosyl)uracil (Compound 17)

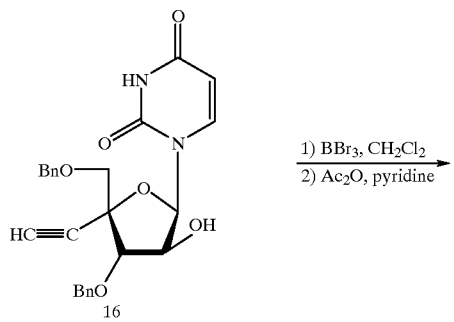

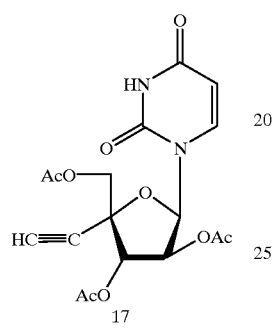

Compound 16 (1.40 g, 3.12 mmol) was dissolved in dichloromethane (40.0 ml), and 1.0 M boron tribromide (15.6 ml, 15.6 mmol) in dichloromethane was added to the solution at −78° C. in an argon atmosphere, followed by stirring for three hours at the same temperature. A mixture of pyridine (5.00 ml) and methanol (10.0 ml) was added thereto at −78° C., and after stirring for ten minutes, the reaction mixture was concentrated through distillation under reduced pressure. After the residue was concentrated by co-boiling with a small amount of methanol three times and by another co-boiling with a small amount of pyridine three times, the residue was dissolved in pyridine (50.0 ml), and acetic anhydride (4.42 ml, 46.7 mmol) was added to the solution, followed by stirring overnight at room temperature. The reaction mixture was brought to dryness under reduced pressure, and the residue was concentrated by co-boiling with a small amount of toluene three times and then partitioned with ethyl acetate and water. The organic layer was dried over anhydrous magnesium sulfate and concentrated through distillation under reduced pressure. The residue was purified by means of silica gel column chromatography (silica gel 150 ml, eluent; chloroform:methanol=20:1), to thereby yield a white powdery compound (Compound 17; 1.15 g, 2.92 mmol, 93.6%).

$^1$H-NMR(CDCl$_3$) δ8.99 (1H, br. s, 3-NH), 7.42 (1H, d, 6-H, $J_{5,6}$=8.24), 6.45 (1H, d, H-1', $J_{1',2'}$=4.95), 5.76 (1H, dd, H-5, $J_{5,6}$=8.24), 5.55 (1H, dd, H-2', $J_{1',2'}$=4.95, $J_{2',3'}$=3.57) 5.34 (1H, d, H-3', $J_{2',3'}$=3.57), 4.51, 4.42 (each 1H, d, H-5', $J_{gem}$=11.81), 2.73 (1H, s, ethynyl).

FABMS m/z: 395(MH$^+$).

HRMS m/z(MH$^+$): Calcd. for C$_{17}$H$_{19}$N$_2$O$_9$: 395.1090, Found: 395.1092.

[α]$_D$ 18.2° (c=1.00, CHCl$_3$).

m.p. 160–162° C.

(5) Synthesis of 1-(4-C-ethynyl-β-D-arabino-pentofuranosyl)cytosine (Compound 19)

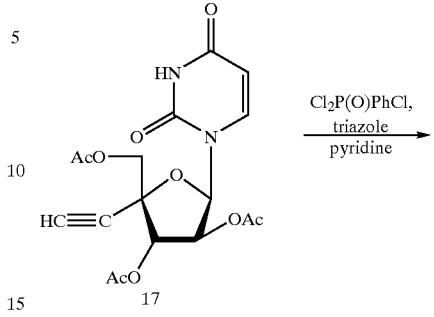

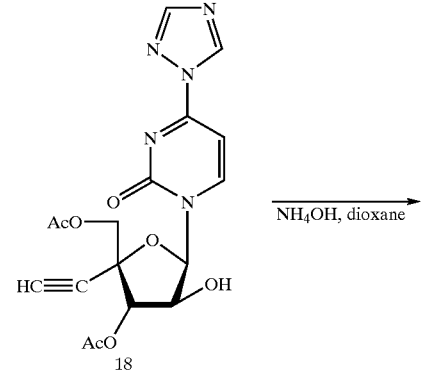

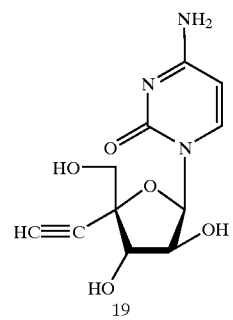

Compound 17 (1.00 g, 2.54 mmol) was dossolved in pyridine (50.0 ml), and p-chlorophenylphosphrodichloridate (1.05 ml, 6.38 mmol) was added to the solution under ice-cooling, followed by stirring for five minutes. 1,2,4-Triazole (1.75 g, 25.3 mmol) was added to the mixture, followed by stirring for seven days at room temperature. After disappearance of raw material had been confirmed by means of silica gel thin-layer chromatography, the reaction mixture was concentrated through distillation under reduced pressure, and the residue was partitioned with ethyl acetate and water. The organic layer was dried over anhydrous magnesium sulfate and concentrated through distillation under reduced pressure. The residue was purified by means of silica gel column chromatography (silica gel 50 ml, eluent; n-hexane:ethyl acetate=1:3), to thereby yield a colorless viscous compound (Compound 18: 1-(4-C-ethynyl-2,3,5-tri-O-acetyl-β-D-arabino-pentofuranosyl)-4-(1,2,4-triazolo)uracil. Compound 18 was dissolved in dioxane (60.0 ml), and a 25% aqueous solution of ammonia (20.0 ml) was added to the solution, followed by stirring overnight at room temperature. After disappearance of Compound 18 had been confirmed by means of silica gel thin-layer chromatography, the reaction mixture was concentrated through distillation under reduced pressure. The residue was purified by means of reversed-phase medium-pressure column chromatography (Wakosil 40C18 50 g, eluent; a 3% aqueous solution of acetonitrile). The fractions containing Compound 19 were brought to dryness under reduced pressure, and the residue was dissolved in methanol-ether and crystallized from the same medium, to thereby yield a white crystalline compound (Compound 19; 0.51 g, 1.91 mmol, 75.2%).

$^1$H-NMR(DMSO-d$_6$) δ7.52 (1H, d, H-6, $J_{5,6}$=7.42), 7.10 (2H, br. d, NH$_2$), 6.17 (1H, dd, H-1', $J_{1',2'}$=6.04), 5.66 (1H, d, H-5, $J_{5,6}$=7.42), 5.62, 5.49 (each 1H, d, 2'-OH, 3'-OH), 5.42 (1H, t, 5'-OH), 4.16 (1H, q, H-2', $J_{1',2'}$=$J_{2',3'}$=6.04), 3.97 (1H, t, H-3', $J_{2',3'}$=6.04), 3.58 (2H, m, H-5'), 3.48 (1H, s, ethynyl).

$[\alpha]_D$+95.7° (c=1.00, CH$_3$OH)

FABMS m/z: 268(MH$^+$).

HRMS m/z(MH$^+$): Calcd. for C$_{11}$H$_{14}$N$_3$O$_5$: 268.0933, Found: 268.0965.

UV $\lambda_{max}$ (CH$_3$OH) nm (ε): 271 (9350)

m.p. ~200° C. (Dec)

Synthesis Example 4

5-Fluorouracil, 5-ethyluracil, 5-bromovinyluracil, and 5-ethynyluracil were employed instead of uracil used in Synthesis Example 3 (2), and the reactions were carried out in the same manner as described above (if necessary, amination reaction by use of triazole described in (5) was omitted), to thereby synthesize the following compounds:

1-(4-C-ethynyl-β-D-arabino-pentofuranosyl)-5-fluorouracil;

1-(4-C-ethynyl-β-D-arabino-pentofuranosyl)-5-ethyluracil;

1-(4-C-ethynyl-β-D-arabino-pentofuranosyl)-5-bromovinyluracil;

1-(4-C-ethynyl-β-D-arabino-pentofuranosyl)-5-ethynyluracil;

1-(4-C-ethynyl-β-D-arabino-pentofuranosyl)-5-fluorocytosine;

1-(4-C-ethynyl-β-D-arabino-pentofuranosyl)-5-ethylcytosine;

1-(4-C-ethynyl-β-D-arabino-pentofuranosyl)-5-bromovinylcytosine; and 1-(4-C-ethynyl-β-D-arabino-pentofuranosyl)-5-ethynylcytosine.

Synthesis Example 5

(1) Synthesis of 2'-O-acetyl-3',5'-di-O-benzyl-4'-C-triethylsilylethynyladenosine (Compound 20)

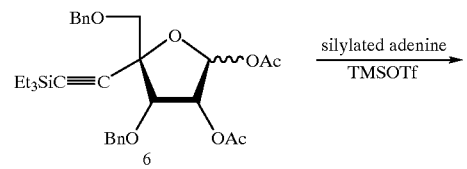

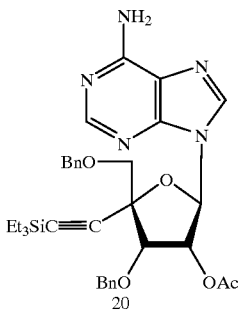

To a solution of Compound 6 (1.1 g, 2 mmol) in 1,2-dichloroethane (16.5 ml), adenine (0.405 g, 3 mmol) and N,O-bis(trimethylsilyl)acetamide (2.7 ml, 11 mmol) were added, followed by refluxing for 1.5 hours. After the mixture was allowed to cool to room temperature, trimethylsilyl trifluoromethanesulfonate (0.77 ml, 4 mmol) was added dropwise to the mixture under stirring at 0° C. in an argon atmosphere. The mixture was stirred for 15 minutes at room temperature, refluxed for 24 hours, and allowed to cool to room temperature. A saturated aqueous solution of sodium hydrogencarbonate was added thereto at 0° C., followed by stirring for 15 minutes at room temperature. Insoluble materials were removed through filtration by use of Celite, and then the organic layer was separated from the filtrate. After an aqueous layer was extracted with chloroform, the organic layer was washed once with a saturated aqueous solution of sodium hydrogencarbonate, dried over anhydrous sodium sulfate, and concentrated through distillation under reduced pressure, so as to evaporate the solvent. The residue was applied to a silica gel column (15 g, eluent; ethyl acetate:n-hexane:ethanol=20:20:1), to thereby yield Compound 20 in an amount of 0.69 g (55%).

$^1$H-NMR(CDCl$_3$) δ8.32 (1H, s, purine-H), 8.01 (1H, s, purine-H), 7.27-7.37 (10H, m, 2×Ph), 6.37 (1H, d, J=5.1 Hz, H-1'), 5.60 (1H, t, J=5.6 Hz, H-2'), 5.59 (2H, br s, NH$_2$), 4.75 (1H, d, J=11.0 Hz, C$\underline{H}$H'Ph), 4.69 (1H, d, J=5.6 Hz, H-3'), 4.60 (1H, d, J=11.0 Hz, CH$\underline{H}$'Ph), 4.58 (1H, d, J=11.2 Hz, C$\underline{H}$H'Ph), 4.51 (1H, d, J=11.0 Hz, CH$\underline{H}$'Ph), 3.84 (1H, d, J=11.1 Hz, H-5'), 3.69 (1H, d, J=11.1 Hz, H-5') 2.03 (3H, s, Ac), 0.98 (9H, t, J=8.7 Hz, 3×C$\underline{H_3}$CH$_2$), 0.61 (6H, q, J=8.7 Hz, 3×CH$_3$C$\underline{H_2}$).

(2) Synthesis of 3',5'-di-O-benzyl-4'-C-triethylsilylethynyladenosine (Compound 21)

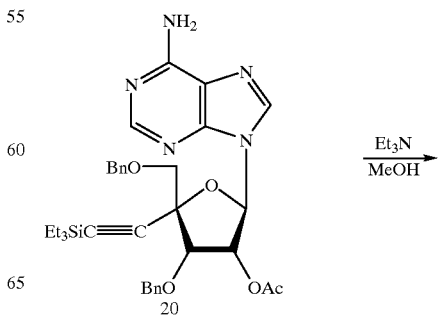

-continued

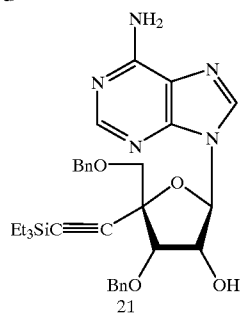
21

To a solution of Compound 20 (0.354 g, 0.565 mmol) in methanol (14 ml), triethylamine (3.3 ml) was added, and the mixture was stirred for one day at room temperature under air-tight condition. The mixture was concentrated under reduced pressure. The residue was applied to a silica gel column (10 g, eluent; ethyl acetate:n-hexane:ethanol 20:10:1), to thereby yield Compound 21 in an amount of 0.283 g (86%).

$^1$H-NMR(CDCl$_3$) δ8.30 (1H, s, purine-H), 8.00 (1H, s, purine-H), 7.30–7.42 (10H, m, 2×Ph), 6.17 (1H, d, J=5.6 Hz, H-1'), 5.55 (2H, br s, NH$_2$), 4.97 (1H, d, J=11.1 Hz, CH̲H'Ph), 4.75–4.80 (1H, m, H-2'), 4.72 (1H, d, J=11.1 Hz, CHH̲'Ph), 4.59 (1H, d, J=11.6 Hz, CH̲H'Ph), 4.54 (1H, d, J=11.6 Hz, CHH̲'Ph), 4.50 (1H, d, J=5.6 Hz, H-3'), 3.84 (1H, d, J=11.1 Hz, H-5'), 3.74 (1H, d, J=11.1 Hz, H-5'), 3.50 (1H, d, J=8.3 Hz, OH), 0.98 (9H, t, J=7.9 Hz, 3×CH$_3$CH$_2$), 0.62 (6H, q, J=7.9 Hz, 3×CH$_3$CH̲$_2$).

(3) Synthesis of 3',5'-di-O-benzyl-2'-deoxy-4'-C-triethylsilylethynyladenosine (Compound 22)

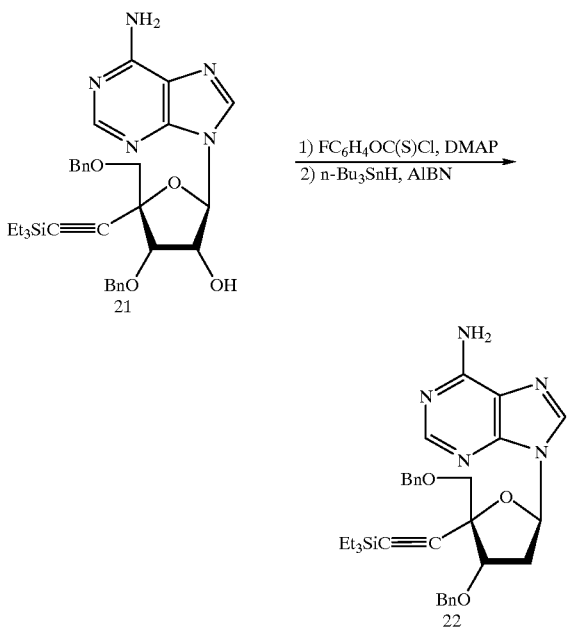

To a solution of Compound 21 (0.18 g, 0.308 mmol) and DMAP (0.113 g, 0.924 mmol) in acetonitrile (10.6 ml), 4-fluorophenylchlorothionoformate (0.065 ml, 0.462 mmol) was added dropwise under stirring at room temperature in an argon atmosphere and stirred for an hour at room temperature, followed by condensation under reduced pressure. Water was added to the residue, and the mixture was extracted with ethyl acetate. The organic layer was washed with water and was washed with a saturated aqueous solution of sodium chloride, dried over anhydrous sodium sulfate, and the solvent was distilled off under reduced pressure. The residue was applied to a silica gel column (eluent; ethyl acetate:n-hexane:ethanol=20:20:1), to thereby yield crude thiocarbonate.

The thiocarbonate was dissolved in toluene (9 ml), and hydrogenated tributyltin (0.41 ml, 1.85 mmol) and 2,2'-azobis(isobutyronitrile) (0.013 g, 0.077 mmol) were added to the solution. The reaction mixture was stirred at 85° C. for an hour in an argon atmosphere and allowed to cool to room temperature. The solvent was evaporated under reduced pressure. The residue was applied to a silica gel column (20 g, eluent; ethyl acetate:n-hexane:ethanol=20:10:1), to thereby yield Compound 22 in an amount of 0.10 g (57%).

$^1$H-NMR(CDCl$_3$) δ8.32 (1H, s, purine-H), 8.11 (1H, s, purine-H), 7.26–7.37 (10H, m, 2×Ph), 6.51 (1H, t, J=6.0 Hz, H-1'), 5.54 (2H, br s, NH$_2$), 4.72 (1H, d, J=12.0 Hz, CH̲H'Ph), 4.61 (2H, d, J=10.5 Hz, CH$_2$Ph), 4.60 (1H, t, J=6.6 Hz, H-3'), 4.55 (1H, d, J=12.0 Hz, CHH̲'Ph), 3.88 (1H, d, J=10.7 Hz, H-5'), 3.76 (1H, d, J=10.7 Hz, H-5'), 2.71–2.76 (2H, m, H-2'), 0.99 (9H, t, J=7.8 Hz, 3×CH$_3$CH$_2$), 0.62 (6H, q, J=7.5 Hz, 3×CH$_3$CH̲$_2$).

(4) Synthesis of 2'-deoxy-4'-C-ethynyladenosine (Compound 23) and 9-(2-deoxy-4-C-ethynyl-β-D-ribofuranosyl)purine (Compound 24)

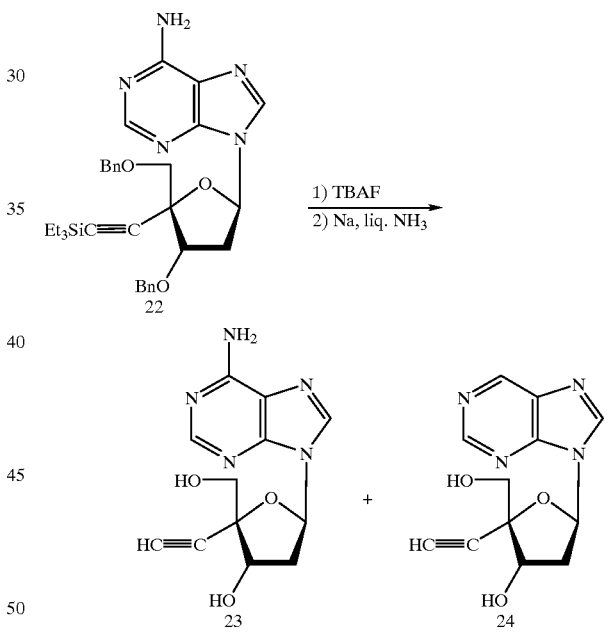

To a solution of Compound 22 (0.23 g, 0.404 mmol) in tetrahydrofuran (9.4 ml), a 1.0 M solution of tetrabutylammonium fluoride (0.44 ml, 0.44 mmol) was added under stirring at room temperature, and after stirring for 30 minutes at the same temperature, the solvent was evaporated under reduced pressure. The residue was applied to a silica gel column and eluted with ethyl acetate, to thereby yield 0.186 g of a crude compound with no triethylsilyl group.

A solution of the above-described compound with no triethylsilyl group in tetrahydrofuran (1.8 ml) and anhydrous ethanol (0.18 ml) were fed to a flask. Ammonia gas was condensed at −78° C. to 18 ml and fed to the flask. Metallic sodium (0.047 g, 2.02 mmol) were added quickly in an argon atmosphere, followed by stirring for 15 minutes at the same temperature. In addition, metallic sodium (0.023 g) was added to the mixture, and after stirring for 10 minutes, ammonium chloride was added. After the mixture was stirred for 1.5 hours at room temperature, ethanol was added thereto. Insoluble materials were separeted through Celite, and washed with ethanol two times. The resultant filtrate and the washing liquid were concentrated under reduced pressure. The residue was applied to a silica gel column (10 g, eluent; ethyl acetate:methanol=20:1), to thereby yield a mixture of Compound 23 and Compound 24 in an amount of 0.079 g. Subsequently, the mixture was applied to a reversed-phase ODS silica gel column and eluted with a 5% aqueous solution of ethanol, to thereby yield Compound 24 in an amount of 0.028 g (27%), and further eluted with a 7.5% aqueous solution of ethanol, to thereby yield Compound 23 in an amount of 0.021 g (19%).

(Compound 23)

$^1$H-NMR(DMSO-d$_6$) δ8.33 (1H, s, purine-H), 8.15 (1H, s, purine-H), 7.30 (2H, br s, NH$_2$), 6.36 (1H, t, J=6.4 Hz, H-1'), 5.54 (1H, d, J=5.4 Hz, OH), 5.53 (1H, t, J=5.4 Hz, OH), 4.58 (1H, q, J=5.9 Hz, H-3'), 3.66 (1H, dd, J=12.2, 5.4 Hz, H-5'), 3.56 (1H, dd, J=11.7, 7.3 Hz, H-5'), 3.50 (1H, s, ethynyl-H), 2.76 (1H, dt, J=13.2, 6.4 Hz, H-2'), 2.41 (1H, dt, J=13.2, 6.8 Hz, H-2').

(Compound 24)

$^1$H-NMR(DMSO-d$_6$) δ9.18 (1H, s, purine-H), 8.96 (1H, s, purine-H), 8.79 (1H, s, purine-H), 6.50 (1H, t, J=7.3, 4.9 Hz, H-1'), 5.60 (1H, d, J=5.9 Hz, OH), 5.29 (1H, t, J=5.4 Hz, OH), 4.67 (1H, q, J=5.9 Hz, H-3'), 3.67 (1H, dd, J=11.7, 5.9 Hz, H-5'), 3.58 (1H, dd, J=11.7, 6.8 Hz, H-5'), 3.53 (1H, s, ethynyl-H), 2.85 (1H, ddd, J=13.2, 6.8, 4.9 Hz, H-2'), 2.48–2.56 (1H, m, H-2').

Synthesis Example 6

(1) Synthesis of 9-(2-O-acetyl-3,5-di-O-benzyl-4-C-triethylsilylethynyl-β-D-ribofuranosyl)-2,6-diaminopurine (Compound 25)

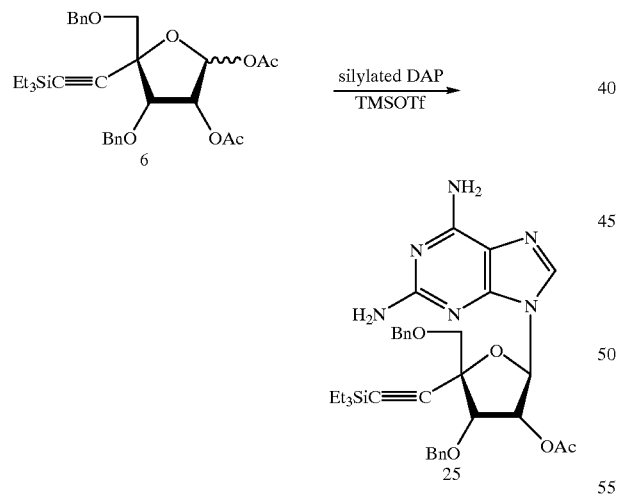

To a solution of Compound 6 (1.1 g, 2 mmol) in 1,2-dichloroethane (16.5 ml), diaminopurine (0.45 g, 3 mmol) and N,O-bis(trimethylsilyl)acetamide (4.4 ml, 18 mmol) were added, followed by refluxing for three hours. After the mixture was cooled to room temperature, trimethylsilyl trifluoromethanesulfonate (0.77 ml, 4 mmol) was added dropwise to the mixture at 0° C. in an argon atmosphere. The mixture was stirred for 15 minutes at room temperature, refluxed for 24 hours, and cooled to room temperature. A saturated aqueous solution of sodium hydrogencarbonate was added thereto at 0° C., followed by stirring for 15 minutes at room temperature. Insoluble materials were separated through filtration by use of Celite, and then the organic layer was separated from the filtrate. After an aqueous layer was extracted with chloroform once, the organic layer was washed with a saturated aqueous solution of sodium chloride, dried over anhydrous sodium sulfate, and the solvent was evaporated under reduced pressure. The residue was applied to a silica gel column (20 g, eluent; ethyl acetate:n-hexane:ethanol=20:10:1), to thereby yield Compound 25 in an amount of 0.85 g (66%).

$^1$H-NMR (CDCl$_3$) δ7.68 (1H, s, H-8), 7.26–7.37 (10H, m, 2×Ph), 6.17 (1H, d, J=6.5 Hz, H-1'), 5.78 (1H, dd, J=6.5, 6.0 Hz, H-2'), 5.34 (2H, br s, NH$_2$), 4.76 (1H, d, J=11.4 Hz, CHH'Ph), 4.69 (1H, d, J=6.0 Hz, H-3'), 4.61 (1H, d, J=11.4 Hz, CHH'Ph), 4.60 (1H, d, J=11.9 Hz, CHH'Ph), 4.55 (2H, br s, NH$_2$), 4.52 (1H, d, J=11.9 Hz, CHH'Ph), 3.83 (1H, d, J=10.7 Hz, H-5'), 3.70 (1H, d, J=10.7 Hz, H-5'), 2.04 (3H, s, Ac), 0.99 (9H, t, J=8.3 Hz, 3×CH$_3$CH$_2$), 0.61 (6H, q, J=8.3 Hz, 3×CH$_3$CH$_2$).

(2) Synthesis of 2,6-diamino-9-(3,5-di-O-benzyl-4-C-triethylsilylethynyl-β-D-ribofuranosyl)purine (Compound 26)

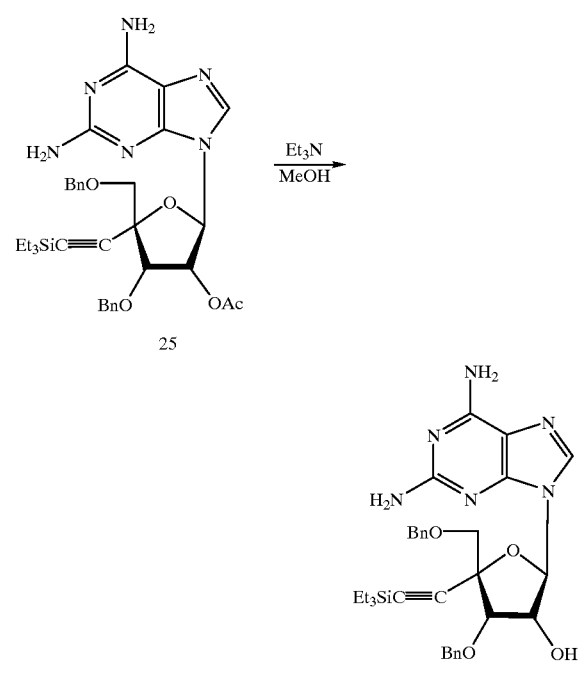

Compound 25 (0.85 g, 1.32 mmol) was treated in the same manner as in the synthesis of Compound 21, and the resultant residue was applied to a silica gel column (15 g, eluent; ethyl acetate:n-hexane:ethanol=30:10:1), to thereby yield Compound 26 in an amount of 0.74 g (93%).

$^1$H-NMR(CDCl$_3$) δ7.70 (1H, s, H-8), 7.29–7.42 (10H, m, 2×Ph), 6.00 (1H, d, J=4.9 Hz, H-1'), 5.35 (2H, br s, NH$_2$), 4.93 (1H, d, J=11.5 Hz, CHH'Ph), 4.74 (1H, d, J=11.5 Hz, CHH'Ph), 4.73 (1H, t, J=5.8 Hz, H-2'), 4.60 (1H, d, J=12.0 Hz, CHH'Ph), 4.55 (2H, br s, NH$_2$), 4.54 (1H, d, J=12.0 Hz, CHH'Ph), 4.49 (1H, d, J=5.9 Hz, H-3'), 3.81 (1H, d, J=10.7 Hz, H-5'), 3.72 (1H, d, J=10.7 Hz, H-5'), 3.62 (1H, br s, OH), 0.99 (9H, t, J=7.8 Hz, 3×CH$_3$CH$_2$), 0.62 (6H, q, J=7.8 Hz, 3×CH$_3$CH$_2$).

(3) Synthesis of 2,6-diamino-9-(3,5-di-O-benzyl-2-deoxy-4-C-triethylsilylethynyl-β-D-ribofuranosyl)purine (Compound 27)

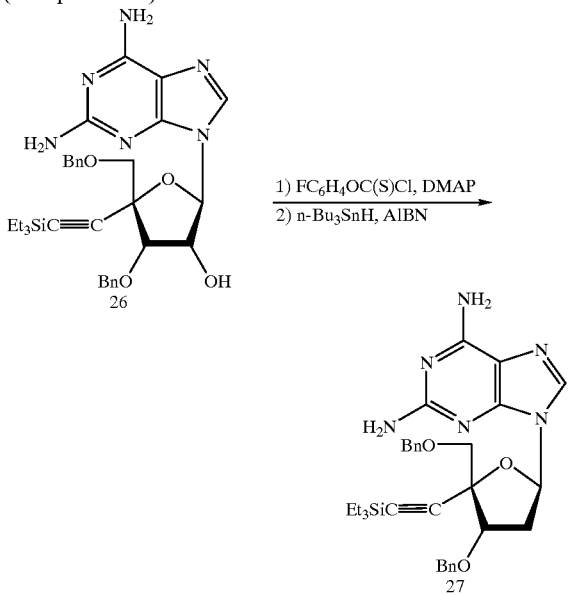

Compound 26 (0.103 g, 0.171 mmol) was treated in the same manner as in the synthesis of Compound 22, and the resultant residue was applied to a silica gel column (10 g, eluent; ethyl acetate:n-hexane:ethanol=30:10:1), to thereby yield Compound 27 in an amount of 0.055 g (55%).

$^1$H-NMR(CDCl$_3$) δ7.79 (1H, s, H-8), 7.26–7.37 (10H, m, 2×Ph), 6.34 (1H, dd, J=6.6, 5.5 Hz, H-1'), 5.36 (2H, br s, NH$_2$), 4.72 (1H, d, J=11.7 Hz, CHH'Ph), 4.56–4.63 (5H, m, CH$_2$Ph, H-3'), 4.57 (1H, d, J=11.7 Hz, CHH'Ph), 3.85 (1H, d, J=10.1 Hz, H-5'), 3.75 (1H, d, J=10.6 Hz, H-5'), 2.62–2.73 (2H, m, H-2'), 0.99 (9H, t, J=7.9 Hz, 3×CH'CH$_2$), 0.62 (6H, q, J=7.9 Hz, 3×CH$_3$CH$_2$).

(4) Synthesis of 2,6-diamino-9-(2-deoxy-4-C-ethynyl-β-D-ribofuranosyl)purine (Compound 28)

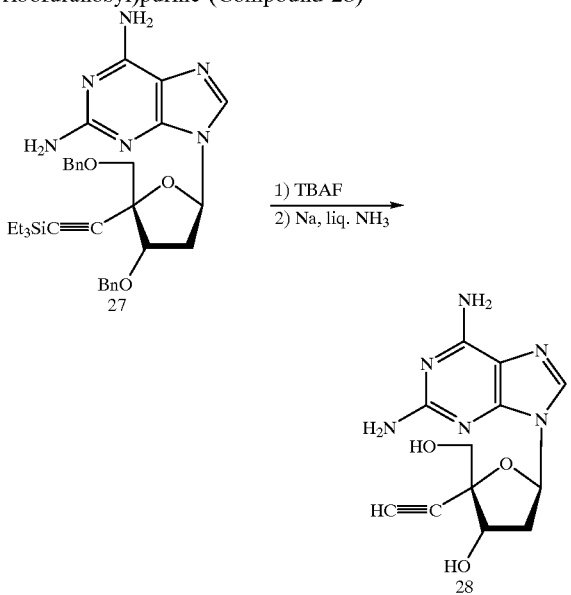

To a solution of Compound 27 (0.263 g, 0.45 mmol) in tetrahydrofuran (10.3 ml), a 1.0 M solution of tetrabutylam monium fluoride (0.5 ml, 0.5 mmol) was added at room temperature, and the mixture was stirred for 30 minutes at the same temperature. The solvent was evaporated under reduced pressure. The residue was applied to a short silica gel column (eluent; ethyl acetate:ethanol=30:1), to thereby yield 0.214 g of a crude compound with no triethylsilyl group.

The above-described compound with no triethylsilyl group in tetrahydrofuran (2 ml) and anhydrous ethanol (0.1 ml) were fed to a flask. Ammonia gas was condensed at −78° C. to 20 ml and fed to the flask. Metallic sodium (0.062 g, 2.7 mmol) was added quickly in an argon atmosphere, followed by stirring for 30 minutes at the same temperature. After ammonium chloride was added thereto, the mixture was stirred for two hours at room temperature, and ethanol was added to the mixture. Insoluble materials were separated through filtration by use of Celite and washed with ethanol two times. The resultant filtrate and the washing liquid were concentrated under reduced pressure. The residue was applied to a silica gel column (13 g, eluent; ethyl acetate:methanol=10:1), to thereby yield Compound 28 in an amount of 0.099 g (76%).

$^1$H-NMR(DMSO-d$_6$) δ7.89 (1H, s, H-8), 6.71 (2H, br s, NH$_2$), 6.20 (1H, t, J=6.3 Hz, H-1'), 5.74 (2H, br s, NH$_2$), 5.59 (1H, t, J=5.9 Hz, OH), 5.47 (1H, d, J=4.9 Hz, OH), 4.50 (1H, q, J=5.9 Hz, H-3'), 3.65 (1H, dd, J=11.7, 5.4 Hz, H-5'), 3.56 (1H, dd, J=11.7, 7.3 Hz, H-5'), 3.46 (1H, s, ethynyl-H), 2.64 (1H, dt, J=12.7, 6.4 Hz, H-2'), 2.32 (1H, dt, J=13.2, 6.4 Hz, H-2').

Synthesis Example 7

Synthesis of 2'-deoxy-4'-C-ethynylinosine (Compound 29)

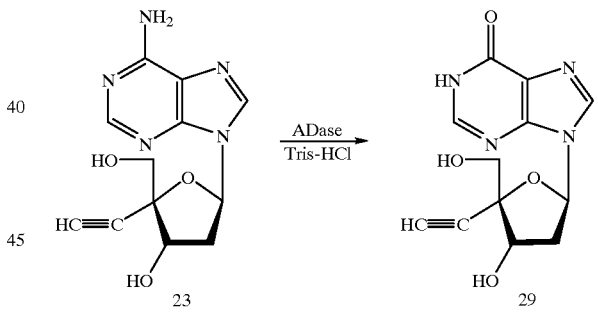

To a Tris-HCl buffer solution (6 ml, pH 7.5) of Compound 23 (0.022 g, 0.08 mmol), adenosine deaminase (0.044 ml, 20 unit) was added, and the mixture was stirred for 2.5 hours at 40° C., followed by cooling to room temperature. The reaction mixture was applied to a reverse-phase ODS silica gel column (50 g), desalted by water (500 ml) flow, and through use of a 2.5% aqueous ethanol, Compound 29 was eluted. Subsequently, the Compound 29 was pulverized with isopropanol, to thereby yield 0.016 g of Compound 29 (72%).

$^1$H-NMR (DMSO-d$_6$) δ12.28 (1H, brs, NH), 8.29 (1H, s, purine-H), 8.06 (1H, s, purine-H), 6.32 (1H, dd, J=6.8, 4.9 Hz, H-1'), 5.57 (1H, d, J=5.4 Hz, OH), 5.32 (1H, t, J=5.9 Hz, OH), 4.56 (1H, dt, J=6.4, 5.4 Hz, H-3'), 3.65 (1H, dd, J=12.2, 5.9 Hz, H-5'), 3.57 (1H, dd, J=11.7, 6.4 Hz, H-5'), 3.50 (1H, s, ethynyl-H), 2.66 (1H, dt, J=12.2, 5.9 Hz, H-2'), 2.46 (1H, dt, J=13.2, 6.9 Hz, H-2').

Synthesis Example 8

Synthesis of 2'-deoxy-4'-C-ethynylguanosine (Compound 30)

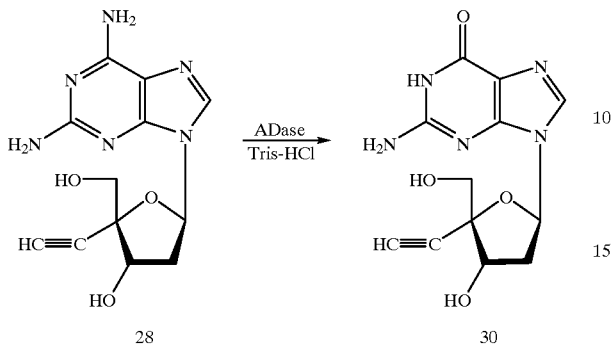

To a Tris-HCl buffer solution (7.8 ml, pH 7.5) of Compound 28 (0.03 g, 0.103 mmol), adenosine deaminase (0.057 ml, 20 unit) was added, and the mixture was stirred for 2 hours at 40° C., followed by cooling to room temperature. The reaction mixture was applied to a reverse-phase ODS silica gel column (50 g), desalted by water (500 ml) flow, and through use of aqueous 2.5% ethanol, Compound 30 was eluted. Recrystallization from water yielded Compound 30 in an amount of 0.015 g (50%).

$^1$H-NMR(DMSO-$d_6$) δ10.61 (1H, br s, NH), 7.90 (1H, s, H-8), 6.48 (2H, br s, NH$_2$), 6.13 (1H, dd, J=7.3, 5.9 Hz, H-1'), 5.51 (1H, d, J=4.9 Hz, OH), 5.30 (1H, t, J=5.9 Hz, OH), 4.47 (1H, dt, J=6.4, 5.4 Hz, H-3'), 3.62 (1H, dd, J=12.2, 6.4 Hz, H-5'), 3.54 (1H, dd, J=12.2, 6.4 Hz, H-5'), 3.47 (1H, s, ethynyl-H), 2.56 (1H, dt, J=12.2, 6.4 Hz, H-2'), 2.36 (1H, dt, J=12.7, 6.8 Hz, H-2').

Synthesis Example 9

Adenine, guanine, and 2,6-diaminopurine were employed instead of uracil used in Synthesis Example 3 (2), and reaction is carried out in a manner similar to that described above (amination by use of triazole described in (5) omitted), to thereby synthesize the following compounds:

9-(4-C-ethynyl-β-D-arabino-pentofuranosyl)adenine;
9-(4-C-ethynyl-β-D-arabino-pentofuranosyl)guanine; and
9-(4-C-ethynyl-β-D-arabino-pentofuranosyl)-2,6-diaminopurine.

Synthesis Example 10

(1) Synthesis of 2'-O-acetyl-3',5'-di-O-benzyl-4'-C-triethylsilylethynyl-5-fluorouridine (Compound 31)

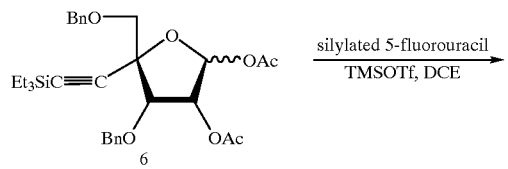

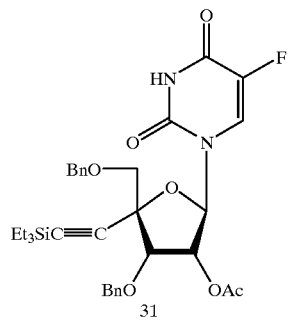

Compound 6 (2.00 g, 3.62 mmol) was dissolved in 1,2-dichloroethane (60.0 ml), and 5-fluorouracil (0.71 g, 5.46 mmol) and N,O-bis(trimethylsilyl)acetamide (5.37 ml, 21.7 mmol) were added to the solution, followed by refluxing for one hour. After the reaction mixture was allowed to cool to room temperature, trimethylsilyl trifluoromethanesulfonate (0.85 ml, 4.70 mmol) was added thereto, followed by stirring overnight at 50° C. A saturated aqueous solution of sodium hydrogencarbonate was added to the mixture, and after stirring, the organic layer was dried over anhydrous magnesium sulfate. The residue was purified by means of silica gel column chromatography (silica gel 300 ml, eluent; n-hexane:ethyl acetate=3:1), to thereby yield a colorless viscous compound (Compound 31; 0.80 g, 1.28 mmol, 35.4%).

$^1$H-NMR(CDCl$_3$) δ7.86 (1H, d, H-6, $J_{6,F}$=6.35), 7.37-7.29 (10H, m, aromatic), 6.32 (1H, dd, H-1', J=5.62, 1.47), 5.17 (1H, t, H-2', $J_{2',3'}$=5.62), 4.73, 4.55 (each 1H, d, benzyl, $J_{gem}$=11.72), 4.55, 4.50 (each 1H, d, benzyl, $J_{gem}$=11.72), 4.32 (1H, d, H-3', $J_{2',3'}$=5.86), 3.87, 3.63 (each 1H, d, H-5 $J_{gem}$=10.50), 2.04 (3H, s, acetyl), 0.96 (9H, t, Si—CH$_2$—CH$_3$, J=8.06), 0.59 (6H, Si—CH$_2$—CH$_3$, J=7.81).

FABMS m/z:623 (MH$^+$).

HRMS m/z(MH$^+$): Calcd. for C$_{33}$H$_{40}$FN$_2$O$_7$Si: 623.2589, Found: 623.2589.

[α]$_D$ –23.3° (c=0.18, CHCl$_3$). ps (2) Synthesis of 3',5'-di-O-benzyl-4'-C-triethylsilylethynyl-5-fluoroouridine (Compound 32):

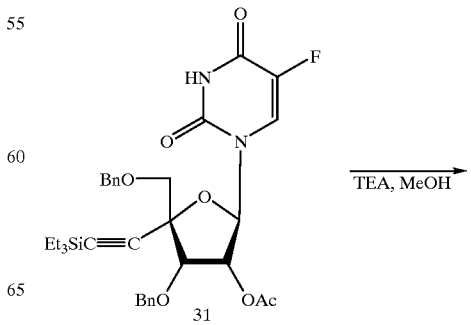

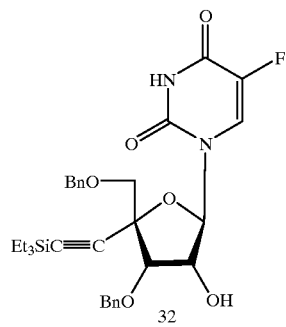

Compound 31 (0.77 g, 1.24 mmol) was dissolved in methanol (45.0 ml), and triethylamine (5.00 ml) was added to the solution, followed by stirring for 48 hours at 30° C. The reaction mixture was concentrated through distillation under reduced pressure, and the residue was purified by means of silica gel column chromatography (silica gel 100 ml, eluent; n-hexane:ethyl acetate=2:1), to thereby yield a white powdery compound (Compound 32; 0.68 g, 1.17 mmol, 94.4%).

$^1$H H-NMR(CDCl$_3$)δ8.42 (1H, br. s, 3-NH), 7.80 (1H, d, $J_{6,F}$=6.10), 7.38-7.29 (10H, m, aromatic), 6.10 (1H, dd, H-1', J=5.98, 1.47), 5.00, 4.63 (each 1H, d, benzyl, $J_{gem}$=11.23), 4.58, 4.54 (each 1H, d, benzyl, $J_{gem}$=10.99), 4.20 (1H, m, H-2'), 4.13 (1H, d, H-3', $J_{2',3'}$=5.86), 3.88, 3.70 (each 1H, d ,H-5', $J_{gem}$=10.25), 2.99 (1H, d, 2'-OH, J=9.77), 0.96 (9H, t, Si—CH$_2$—CH$_3$, J=8.06), 0.58 (6H, Si—CH$_2$—CH$_3$, J=7.82).

FABMS m/z: 581 (MH$^+$).

HRMS m/z(MH$^+$): Calcd. for C$_{31}$H$_{38}$FN$_2$O$_6$Si:581.2483, Found:581.2484.

[α]$_D$–16.3° (c=1.05, CHCl$_3$)

m.p. 138–139° C.

(3) Synthesis of 4'-C-triethylsilylethynyl-5-fluorouridine (Compound 33):

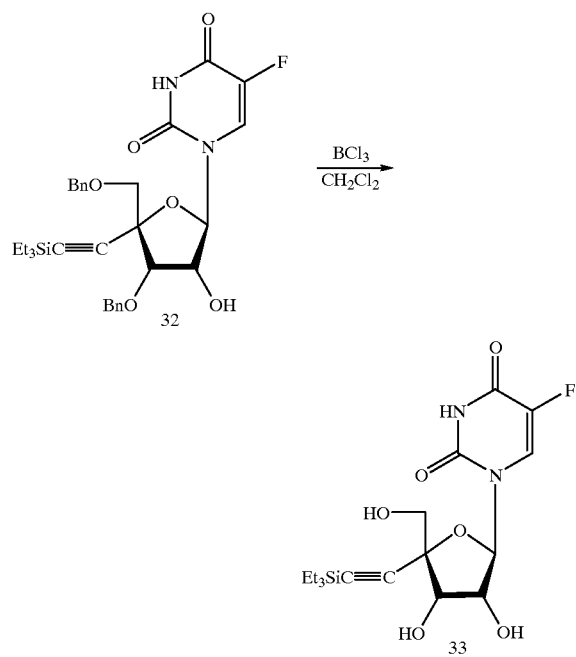

Compound 32 (1.00 g, 1.72 mmol) was dissolved in dichloromethane (50.0 ml), and a solution (26.7 ml, 26.7 mmol) of 1.0 M boron trichloride in dichloromethane was added thereto at −78° C. in an argon atmosphere, followed by stirring for three hours at the same temperature. A mixture of pyridine (10.0 ml) and methanol (20.0 ml) was added at −78° C., followed by stirring for 30 minutes. The reaction mixture was concentrated through distillation under reduced pressure, and the residue was partitioned with ethyl acetate and water. The organic layer was dried over anhydrous magnesium sulfate and concentrated through distillation under reduced pressure. The residue was purified by means of silica gel column chromatography (silica gel 150 ml, eluent; chloroform:methanol=10:1), to thereby yield a white powdery compound (Compound 33; 0.64 g, 1.60 mmol, 93.0%).

$^1$H-NMR(DMSO-d$_6$) δ11.93 (1H, d, 3-NH, J=5.13), 8.13 (1H, d, H-6, $J_{6,F}$=7.08), 5.89 (1H, dd, H-1', J=6.35,1.95), 5.71 (1H, t, 5'-OH, J=5.37), 5.37, 5.23 (each 1H, d, 2'-OH, 3'-OH, J=6.35), 4.12 (1H, q, H-2, J=6.35), 4.05 (1H, t, H-3, J=5.61), 3.61-3.57 (2H, m, H-5), 3.35 (1H, s, ethynyl), 0.95 (9H, t, Si—CH$_2$—CH$_3$, J=7.81), 0.55 (6H, Si—CH$_2$—CH$_3$, J=7.81).

FABMS m/z: 401 (MH$^+$).

HRMS m/z(MH$^+$): Calcd. for C$_{17}$H$_{26}$FN$_2$O$_6$Si: 401.1544, Found:401.1550.

[α]$_D$–2.30° (c=1.00,CH$_3$OH)

m.p. 180–183° C.

(4) Synthesis of 3',5'-di-O-acetyl-2'-deoxy-4'-C-triethylsilylethynyl-5-fluorouridine (Compound 34):

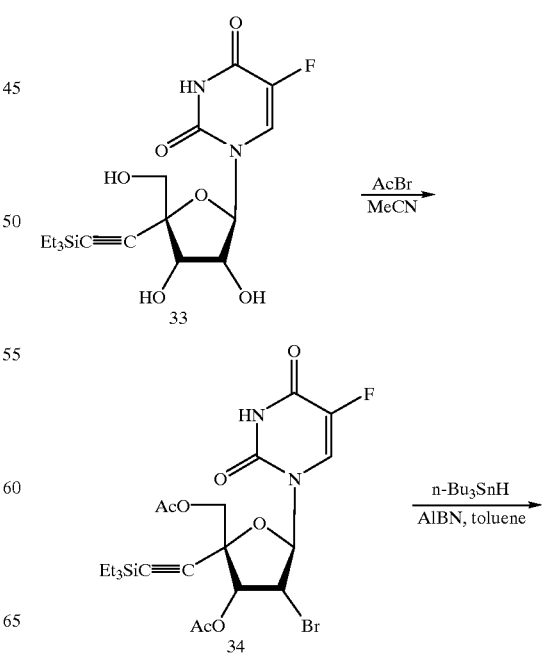

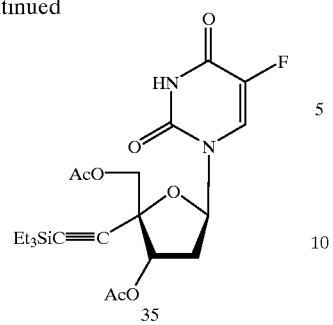

Compound 33 (0.54 g, 1.35 mmol) was suspended in acetonitrile (30.0 ml), and a solution (20.0 ml) of acetyl bromide (1.00 ml, 13.5 mmol) in acetonitrile was added dropwise to the suspension at 85° C. over one hour, followed by refluxing for a further three hours. After the reaction mixture was concentrated through distillation under reduced pressure, the residue was dissolved in ethyl acetate and the solution was washed sequentially with a saturated aqueous sodium hydrogencarbonate solution and a saturated aqueous sodium chloride solution. The organic layer was dried over anhydrous magnesium sulfate and concentrated through distillation under reduced pressure, to thereby yield 3',5'-di-O-acetyl-2'-bromo-2'-deoxy-4'-C-triethylsilylethynyl-5-fluorouridine in crude form (Compound 34). After the crude product (Compound 34) was concentrated by co-boiling with toluene three times, the product was dissolved in dry toluene (20.0 ml). Hydrogenated tri(n-butyl)tin (0.75 ml, 2.91 mmol) and 2,2'-azobis(isobutyronitrile) (0.01 g) were added to the solution at 85° C., and the mixture was heated under stirring for 30 minutes in an argon atmosphere. After the reaction mixture was concentrated through distillation under reduced pressure, the residue was purified by means of silica gel column chromatography (silica gel 200 ml, eluent; n-hexane ethyl acetate), to thereby yield a white powdery compound (Compound 35; 0.41 g, 0.88 mmol, 65.2%).

$^1$H-NMR(CDCl$_3$)δ9.23 (1H, br.s, 3-NH), 7.70 (1H, d, H-6, $J_{6,F}$=6.10), 6.35 (1H, t, H-1', $J_{1',2'}$=7.08), 5.36 (1H, t, H-3', $J_{2',3'}$=7.57), 4.43, 4.39 (each 1H, d, H-5', $J_{gem}$=12.21), 2.65, 2.33 (each 1H, m, H-2'), 2.17, 2.13 (each 3H, s, acetyl), 1.00 (9H, t, Si—CH$_2$—CH$_3$, J=7.82), 0.63 (6H, Si—CH$_2$—CH$_3$, J=7.82).

FABMS m/z: 469 (MH$^+$).

HRMS m/z(MH$^+$): Calcd. for C$_{21}$H$_{30}$FN$_2$O$_7$Si:469.1806, Found: 469.1810.

[α]$_D$−12.9° (c=1.00,CHCl$_3$)

m.p. 111–112° C.

(5) Synthesis of 4'-C-ethynyl-2'-deoxy-5-fluorocytidine (Compound 37)

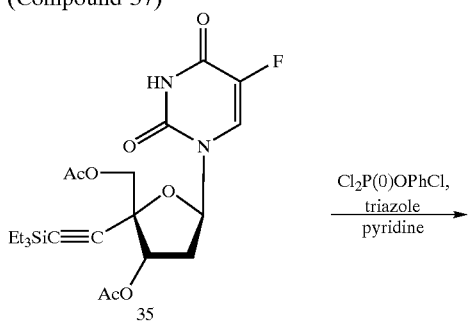

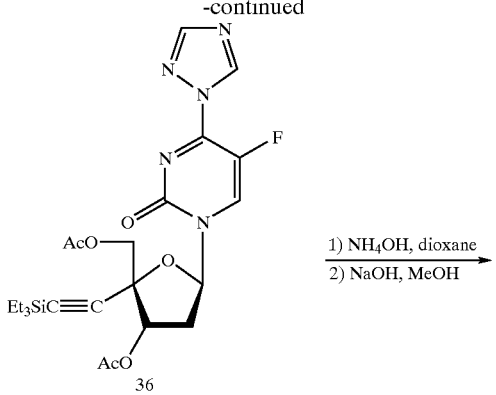

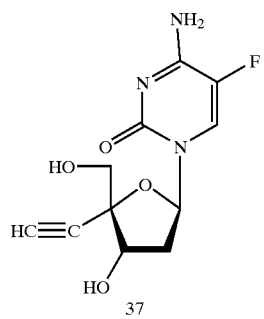

Compound 35 (0.35 g, 0.75 mmol) was dissolved in pyridine (5.00 ml), and p-chlorophenylphosphrodichloridate (0.62 ml, 3.77 mmol) was added to the resultant solution under ice-cooling, followed by stirring for five minutes. 1,2,4-Triazole (0.78 g, 11.3 mmol) was added to the mixture, followed by stirring for 24 hours at 30° C. The reaction mixture was concentrated through distillation under reduced pressure, and the residue was partitioned with ethyl acetate and water. The organic layer was dried over anhydrous magnesium sulfate, and concentrated through distillation under reduced pressure. The residue was purified by means of silica gel column chromatography (silica gel 50 ml, eluent; ethyl acetate), to thereby yield a colorless viscous compound (4'-C-triethylsilylethynyl-2'-deoxy-5-fluoro-4-(1,2,4-triazolo)uridine; Compound 36). Compound 36 was dissolved in dioxane (15.0 ml), and 25% aqueous ammonia (5.00 ml) was added to the resultant solution, followed by stirring overnight at room temperature. After disappearance of Compound 36 had been confirmed by means of silica gel thin-layer chromatography (chloroform:methanol=10:1), the reaction mixture was concentrated through distillation under reduced pressure. The residue was dissolved in methanol (45.0 ml), and an aqueous 1 N sodium hydroxide solution (5.00 ml, 5.00 mmol) was added thereto, followed by stirring for 24 hours at room temperature. Acetic acid (0.29 ml, 5.00 mmol) was added to the mixture, and the reaction mixture was concentrated through distillation under reduced pressure. The residue was purified by means of silica gel column chromatography (silica gel 50 ml; chloroform:ethanol=4:1). The fraction containing Compound 37 was brought to dryness under reduced pressure, and the residue was crystallized from methanol-ether, to thereby yield a white crystalline compound (Compound 37; 0.12 g, 0.45 mmol, 60.0%).

$^1$H-NMR(DMSO-d$_6$) δ8.06 (1H, d, H-6, $J_{6,F}$=7.08), 7.79, 7.54 (each 1H, br.s, NH$_2$), 6.05 (1H, m, H-1'), 5.57, 5.50 (each 1H, br, 3'-OH, 5'-OH), 4.31 (1H, br.q, H-3), 3.66, 3.60 (each 1H, d, H-5, $J_{gem}$=11.72), 3.51 (1H, s, ethynyl), 2.25, 2.12 (each 1H, m, H-2')

$[\alpha]_D$ +77.9° (c=1.00, $CH_3OH$)
FABMS m/z: 270 ($MH^+$).
HRMS m/z($MH^+$): Calcd. for $C_{11}H_{13}FN_3O_4$: 270.0890, Found: 270.0888.
m.p. −225° C. (Dec)

Drug Preparation Example 1

Tablets

| | |
|---|---|
| Compound of the present invention | 30.0 mg |
| Cellulose micropowder | 25.0 mg |
| Lactose | 39.5 mg |
| Starch | 40.0 mg |
| Talc | 5.0 mg |
| Magnesium stearate | 0.5 mg |

Tablets are prepared from the above composition through a customary method.

Drug Preparation Example 2

Encapsulated Drug

| | |
|---|---|
| Compound of the present invention | 30.0 mg |
| Lactose | 40.0 mg |
| Starch | 15.0 mg |
| Talc | 5.0 mg |

Encapsulated drugs are prepared from the above composition through a customary method.

Drug Preparation Example 3

Injections

| | |
|---|---|
| Compound of the present invention | 30.0 mg |
| Glucose | 100.0 mg |

Injections are prepared by dissolving the above composition in purified water for preparing injections.

Test Examples will next be described. Employed in tests were the following seven compounds of the present invention and two known compounds:
Compound 13: 4'-C-ethynyl-2'-deoxycytidine;
Compound 19: 1-(4-C-ethynyl-β-D-arabinopentofuranosyl)cytosine;
Compound 23: 9-(2-deoxy-4-C-ethynyl-β-D-ribopentofuranosyl)adenine (4'-C-ethynyl-2'-deoxyadenosine);
Compound 28: 9-(2-deoxy-4-C-ethynyl-β-D-ribopentofuranosyl)-2,6-diaminopurine;
Compound 29: 9-(2-deoxy-4-C-ethynyl-β-D-ribopentofuranosyl)hypoxanthine (4'-C-ethynyl-2'-deoxyinosine);
Compound 30: 9-(2-deoxy4-C-ethynyl-β-D-ribopentofuranosyl)guanine (4'-C-ethynyl-2'-deoxyguanosine);
Compound 37: 4'-C-ethynyl-2'-deoxy-5-fluorocytidine); and
Known compounds: 4'-C-ethynylthymidine and AZT.

Test Examples

Test Methods (1) Anti-HSV-1 Activity
1. Human embryonic lung cells are subcultured by splitting at 1:2 to 1:4 in an Eagle's MEM supplemented with 10% bovine serum (Mitsubishi Chemical Corporation) at intervals of 4–5 days.
2. The suspension of cells obtained from parent cells by splitting at 1:2 is added to a 96-well-microplate at 200 µl/well, and the cells are cultured in a $CO_2$-incubator for four days at 37° C.
3. After culture medium is removed, a test agent (100 µl) in serial fivefold dilution with a Hanks' MEM is added to the wells.
4. An Eagle's MEM (100 µl) supplemented with 5% bovine serum containing 100–320 $TCID_{50}$ of herpes simplex virus type-1, VR-3 strain is added to the wells to thereby seed the virus, and the infected cells are cultured at 37° C. in a $CO_2$-incubator.
5. After the cells are cultured for 2–3 days, the degree of CPE of each well is observed under a microscope for evaluation on a scale of 0 to 4. When the cells in test agent-free controls are completely degenerated through infection with the virus, the CPE score is 4.
6. The antiviral activity is expressed as $ED_{50}$ at which HSV-induced CPE were expressed at least 50%.

(2) Anti-human Immunodeficiency Virus (HIV) Activity
1) MTT Method Using MT-4 Cells
1. A test agent (100 µl) is diluted on a 96-well microplate. MT-4 cells infected with HIV-1 ($III_b$ strain; 100 $TCID_{50}$) and non-infected MT-4 cells are added to the microplate such that the number of cells in each well becomes 10,000. The cells are cultured at 37° C. for five days.
2. MTT (20 µl, 7.5 mg/ml) is added to each well, and the cells are further cultured for 2–3 hours.
3. The cultured medium (120 µl) is sampled, and MTT terminating solution (isopropanol containing 4% Triton X-100 and 0.04N HCl) is added to the sample. The mixture is stirred to form formazane, which is dissolved. The absorbance at 540 nm of the solution is measured. Since the absorbance is proportional to the number of viable cells, the test agent concentration at which a half value of the absorbance is measured in a test using infected MT-4 cells represents $EC_{50}$, whereas the test agent concentration at which a half value of the absorbance is measured in a test using non-infected MT-4 cells represents $CC_{50}$.

2) MAGI Assay Using HeLa CD4/LTR-beta-Gal Cells
1. HeLa CD4/LTR-beta-Gal cells are added to 96 wells such that the number of cells in each well is 10,000. After 12–24 hours, the culture medium is removed, and a diluted test agent (100 µl) is added.
2. A variety of HIV strains (wild strain: WT, drug-resistant strain: MDR, M184V, NL4-3, 104pre, and C; each equivalent to 50 $TCID_{50}$) are added, and the cells are further cultured for 48 hours.
3. The cells are fixed for five minutes using PBS containing 1% formaldehyde and 0.2% glutaraldehyde.
4. After the fixed cells are washed with PBS three times, the cells are stained with 0.4 mg/ml X-Gal for one hour, and the number of blue-stained cells of each well is counted under a transmission stereoscopic microscope. The test agent concentration at which blue-stained cells decrease to 50% and 90% in number represents $EC_{50}$ and $EC_{90}$, respectively.
5. In a manner similar to that employed in the MTT method, cytotoxicity is measured by use of HeLa CD4/LTR-beta-Gal cells.
The test results are shown in Tables 1 to 7.

Results (1) Anti-HSV-1 Activity

TABLE 1

| Drug | HSV-1(ED$_{50}$, μg/ml) |
|---|---|
| Compound 13 | 33 |

(2) Anti-human Immunodeficiency Virus (HIV) Activity and Cytotoxicity

Each value shown in Tables 2 to 7 represents an average of two to five assayed values.

1. MTT Method Using MT-4 Cells

TABLE 2

| | MT-4 cells | |
|---|---|---|
| Drugs | HIV-1 (EC$_{50}$, μg/ml) | Cytotoxicity (CC$_{50}$, μg/ml) |
| Compound 13 | 0.0012 | 0.56 |
| Compound 19 | 0.0115 | 0.53 |
| 4'-C-ethynyl thymidine | 0.22 | >100 |
| AZT | 0.0016 | >0.27 |

TABLE 3

| | MT-4 cells | |
|---|---|---|
| Drugs | HIV-1 (EC$_{50}$, μg/ml) | Cytotoxicity (CC$_{50}$, μg/ml) |
| Compound 23 | 0.0027 | 4.4 |
| Compound 28 | 0.0001 | 0.26 |
| Compound 29 | 0.037 | 38 |
| Compound 30 | 0.00044 | 0.41 |
| AZT | 0.0011 | 9.08 |

TABLE 4

| | MT-4 cells | |
|---|---|---|
| Drugs | HIV-1 (EC$_{50}$, μM) | Cytotoxicity (CC$_{50}$, μM) |
| Compound 37 | 0.033 | >500 |
| AZT | 0.055 | |

2. MAGI Assay Using HeLa CD4/LTR-beta-Gal Cells

TABLE 5

| | HeLa CD4/LTR-beta-Gal cells | | | |
|---|---|---|---|---|
| | HIV | | | |
| Drugs | WT | MDR (EC$_{50}$, μg/ml) | M184V | Cytotoxicity (CC$_{50}$, μg/ml) |
| Compound 13 | 0.00031 | 0.00030 | 0.00054 | >100 |
| Compound 19 | 0.0019 | 0.021 | 0.19 | >100 |
| 4'-C-ethynyl thymidine | 0.097 | 0.033 | 0.049 | >100 |
| AZT | 0.0059 | 4.1 | 0.0083 | >26.7 |

TABLE 6

| | HeLa CD4/LTR-beta-Gal cells | | | |
|---|---|---|---|---|
| | HIV | | | |
| Drugs | WT | MDR (EC$_{50}$, μg/ml) | M184V | Cytotoxicity (CC$_{50}$, μg/ml) |
| Compound 23 | 0.0012 | 0.0017 | 0.013 | >100 |
| Compound 28 | 0.00028 | 0.00029 | 0.0017 | 2.7 |
| Compound 29 | 0.22 | 0.14 | 4.6 | >100 |
| Compound 30 | 0.002 | 0.0014 | 0.0023 | 15.2 |
| AZT | 0.0027 | 5.34 | 0.0013 | >26.7 |

TABLE 7

| | HeLa CD4/LTR-beta-Gal cells | |
|---|---|---|
| | HIV | |
| Drugs | NL-43 | 104 pre EC$_{50}$, μM (EC$_{90}$, μM) | C |
| Compound 37 | 0.021 (0.25 | 0.022 0.19 | 0.122 3.44) |
| AZT | 0.109 (4.96 | 0.059 9.66 | 3.269 >10) |

What is claimed is:

1. A 4'-C-ethynyl pyrimidine represented by the following formula (1):

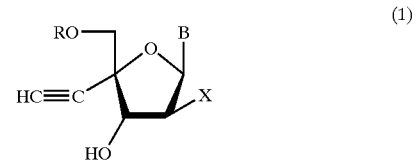

(1)

wherein B represents a pyrimidin-1-yl or a derivative thereof, wherein the derivative is a pyrimidin-1-yl having a substituent selected from the group consisting of a halogen atom, an alkyl group, a haloalkyl group, an alkenyl group, a haloalkyl group, an alkynyl group, an amino group, an alkylamino group, a hydroxy group, a hydroxyamino group, an aminoxy group, an alkoxy group, a mercapto group, an alkylmercapto group, an aryl group, an aryloxy group, and a cyano group, and R represents a hydrogen atom or a phosphate ester group, and X represents a hydrogen atom or a hydroxyl group, or a pharmaceutically acceptable salt, hydrate, or solvate thereof, provided that the compound is not 4'-C-ethynylthymidine, 4'-C-ethynyl-2'-deoxycytidine, 4'-C-ethynyl-2'-deoxy-5-fluorocytidine, or 1-(4'-C-ethynyl-β-D-arabinopentofuranosyl)cytosine.

2. A compound according to claim 1, wherein X is a hydrogen atom.

3. A compound according to claim 1, wherein X is a hydroxyl group.

4. The compound according to claim 1, wherein B is cytosin-1-yl or said derivative thereof.

5. The compound according to claim 1, wherein B is cytosin-1-yl or said derivative thereof, and X is a hydrogen atom.

6. The compound according to claim 1, wherein B is cytosin-1-yl or said derivative thereof, and X is a hydroxyl group.

7. A pharmaceutical composition comprising a 4'-C-ethynyl pyrimidine nucleoside as recited in claim 1 and a pharmaceutically acceptable carrier.

8. A pharmaceutical composition comprising a 4'-C-ethynyl pyrimidine nucleoside as recited in claim 2 and a pharmaceutically acceptable carrier.

9. A pharmaceutical composition comprising a 4'-C-ethynyl pyrimidine nucleoside as recited in claim 3 and a pharmaceutically acceptable carrier.

10. A pharmaceutical composition comprising a 4'-C-ethynyl pyrimidine nucleoside as recited in claim 4 and a pharmaceutically acceptable carrier.

11. A pharmaceutical composition comprising a 4'-C-ethynyl pyrimidine nucleoside as recited in claim 5 and a pharmaceutically acceptable carrier.

12. A pharmaceutical composition comprising a 4'-C-ethynyl pyrimidine nucleoside as recited in claim 6 and a pharmaceutically acceptable carrier.

* * * * *

UNITED STATES PATENT AND TRADEMARK OFFICE
CERTIFICATE OF CORRECTION

PATENT NO.    : 6,403,568 B1                                                Page 1 of 1
DATED         : June 11, 2002
INVENTOR(S)   : Hiroshi Ohrui et al.

It is certified that error appears in the above-identified patent and that said Letters Patent is hereby corrected as shown below:

<u>Column 42,</u>
Line 29, please replace "ethynyl pyrimidine represented" with -- ethynyl pyrimidine nucleoside represented --.

Signed and Sealed this

Twenty-second Day of July, 2003

JAMES E. ROGAN
*Director of the United States Patent and Trademark Office*